US009044431B2

(12) United States Patent
Sanberg et al.

(10) Patent No.: US 9,044,431 B2
(45) Date of Patent: Jun. 2, 2015

(54) METHODS OF TREATING STROKE USING STEM CELL-LIKE MENSTRUAL BLOOD CELLS

(75) Inventors: Paul R. Sanberg, Spring Hill, FL (US); Cesario V. Borlongan, Odessa, FL (US); Julie Allickson, Odessa, FL (US)

(73) Assignees: University of South Florida, Tampa, FL (US); Medical College of Georgia, Augusta, GA (US); Cryo-Cell International, Inc., Oldsmar, FL (US)

( * ) Notice: Subject to any disclaimer, the term of this patent is extended or adjusted under 35 U.S.C. 154(b) by 275 days.

(21) Appl. No.: 13/107,391

(22) Filed: May 13, 2011

(65) Prior Publication Data
US 2011/0268710 A1    Nov. 3, 2011

Related U.S. Application Data

(63) Continuation of application No. PCT/US2009/064379, filed on Nov. 13, 2009.

(60) Provisional application No. 61/114,311, filed on Nov. 13, 2008.

(51) Int. Cl.
*A61K 35/30* (2006.01)
*A61K 35/14* (2006.01)
*A61K 38/18* (2006.01)

(52) U.S. Cl.
CPC .............. *A61K 35/14* (2013.01); *A61K 35/30* (2013.01); *A61K 38/185* (2013.01); *A61K 38/1866* (2013.01)

(58) Field of Classification Search
CPC ... A61K 35/30; A61K 35/545; C12N 5/0634; C12N 5/0623; C12N 5/0665
See application file for complete search history.

(56) References Cited

U.S. PATENT DOCUMENTS

| 2005/0169902 | A1 | 8/2005 | Borlongan et al. |
| 2008/0241113 | A1 | 10/2008 | Walton et al. |
| 2009/0053182 | A1* | 2/2009 | Ichim et al. ............. 424/93.7 |
| 2009/0191628 | A1 | 7/2009 | Walton et al. |

OTHER PUBLICATIONS

Vendrame et al., Cord Blood Rescues Stroke-Induced Changes in Splenocyte Phenotype and Function, Experimental Neurology, 2006, vol. 199, pp. 191-200.
Vescovi et al., Establishment and Properties of Neural Stem Cell Clones: Plasticity In Vitro and In Vivo, Brain Pathology, 1999, vol. 9, pp. 569-598.
Remberger et al., Major ABO Blood Group Mismatch Increases the Risk for Graft Failure After Unrelated Donor Hematopoietic Stem Cell Transplantation, Biology of Blood and Marrow Transplantation, 2007, vol. 13, pp. 675-682.
Virley et al., A Temporal MRI Assessment of Neuropathology After Transient Middle Cerebral Artery Occlusion in the Rat: Correlations with Behavior, Journal of Cerebral Blood Flow and Metabolism, 2000, vol. 20, pp. 563-582.
Wang et al., Neural Progenitor Cells Treated with EPO Induce Angiogenesis Through the Production of VEGF, Journal of Cerebral Blood Flow & Metabolism, 2008, vol. 28, pp. 1361-1368.
Wegener et al., Temporal Profile of T2-Weighted MRI Distinguishes Between Pannecrosis and Selective Neuronal Death After Transient Focal Cerebral Ischemia in the Rat, Journal of Cerebral Blood Flow & Metabolism, 2006, vol. 26, pp. 38-47.
Yasuhara et al., Transplantation of Human Neural Stem Cells Exerts Neuroprotection in a Rat Model of Parkinson's Disease, The Journal of Neuroscience, 2006, vol. 26, No. 48, pp. 12497-12511.
Yasuhara et al., Mannitol Facilitates Neurotrophic Factor Up-Regulation and Behavioural Recovery in Neonatal Hypoxic-Ischaemic Rats with Human Umbilical Cord Blood Grafts, J. Cell. Mol. Med., 2010, vol. 14, No. 4, pp. 914-921.
Yasuhara et al., Notch-Induced Rat and Human Bone Marrow Stromal Cell Grafts Reduce Ischemic Cell Loss and Ameliorate Behavioral Deficits in Chronic Stroke Animals, Stem Cells and Development, 2009, vol. 18, No. 10, pp. 1501-1515.
Yu et al., Amnion: A Potent Graft Source for Cell Therapy in Stroke, Cell Transplantation, 2009, vol. 18, pp. 111-118.
Zhong et al., Feasibility Investigation of Allogeneic Endometrial Regenerative Cells, Journal of Translational Medicine, 2009, vol. 7, pp. 15-21.
Hutchinson et al., GDNF in Parkinson Disease: An Object Lesson in the Tyranny of Type II, Journal of Neuroscience Methods, 2007, vol. 163, pp. 190-192.

(Continued)

Primary Examiner — Robert C Hayes
(74) Attorney, Agent, or Firm — Robert J. Varkonyi; Smith & Hopen, P.A.

(57) ABSTRACT

A cell type that is a complete match of the transplant recipient appears as an optimal scenario to open treatment options to a large patient population with minimal complications. The use of autologous bone marrow or umbilical cord blood has been proposed as a good source of stem cells for cell therapy. Menstrual blood is found to be another important source of stem cells. Assays of cultured menstrual blood reveal that they express embryonic like-stem cell phenotypic markers and neuronal phenotypic markers under appropriate conditioned media. Oxygen glucose deprivation stroke models show that OGD-exposed primary rat neurons, co-cultured with menstrual blood-derived stem cells or exposed to the media from cultured menstrual blood, exhibited significantly reduced cell death. Transplantation of menstrual blood-derived stem cells, either intracerebrally or intravenously, after experimentally induced ischemic stroke in adult rats also significantly reduced behavioral and histological impairments compared to vehicle-infused rats.

13 Claims, 11 Drawing Sheets

(56) References Cited

OTHER PUBLICATIONS

Yasuhara et al., Early Transplantation of an Encapsulated Glial Cell Line-Derived Neurotrophic Factor-Producing Cell Demonstrating Strong Neuroprotective Effects in a Rat Model of Parkinson Disease, J. Neurosurg., 2005, vol. 102, pp. 80-89.

Borlongan, Cell Therapy for Stroke, Remaining Issues to Address Before Embarking on Clinical Trials, Stroke, 2009, vol. 40, Suppl. 1, pp. S146-S148.

The STEPS Participants, Stem Cell Therapies as an Emerging Paradigm in Stroke (STEPS), Bridging Basic and Clinical Science for Cellular and Neurogenic Factor Therapy in Treating Stroke, Stroke, 2009, vol. 40, pp. 510-515.

Xu et al., Oxygen-Glucose Deprivation Induces Inducible Nitric Oxide Synthase and Nitrotyrosine Expression in Cerebral Endothelial Cells, Stroke, 2000, vol. 31, pp. 1744-1751.

Schwarting et al., Hematopoietic Stem Cells Reduce Postischemic Inflammation and Ameliorate Ischemic Brain Injury, Stroke, 2008, vol. 39, pp. 2867-2875.

Sicard et al., Long-Term Changes of Functional MRI-Based Brain Function, Behavioral Status, and Histopathology After Transient Focal Cerebral Ischemia in Rats, Stroke, 2006, vol. 37, pp. 2593-2600.

Malagelada et al., Histamine H2-Receptor Antagonist Ranitidine Protects Against Neural Death Induced by Oxygen-Glucose Deprivation, Stroke, 2004, vol. 35, pp. 2396-2401.

Borlongan et al., Central Nervous System Entry of Peripherally Injected Umbilical Cord Blood Cells is Not Required for Neuroprotection in Stroke, Stroke, 2004, vol. 35, pp. 2385-2389.

Bliss et al., Cell Transplantation Therapy for Stroke, Stroke, 2007, vol. 38, Part 2, pp. 817-826.

Fleischhauer et al., Graft Rejection After Unrelated Donor Hematopoietic Stem Cell Transplantation for Thalassemia is Associated with Nonpermissive HLA-DPB1 Disparity in Host-Versus-Graft Direction, Blood, 2006, vol. 107, No. 7, pp. 2984-2992.

Chang et al., Human Amniotic Fluid Cells Grown in a Hormone-Supplemented Medium: Suitability for Prenatal Diagnosis, Proc. Natl. Acad. Sci. USA, 1982, vol. 79, pp. 4795-4799.

Borlongan et al., Glial Cell Survival is Enhanced During Melatonin-Induced Neuroprotection Against Cerebral Ischemia, FASEB J., 2000, vol. 14, pp. 1307-1317.

Laughlin et al., Outcomes After Transplantation of Cord Blood or Bone Marrow from Unrelated Donors in Adults with Leukemia, The New England Journal of Medicine, 2004, vol. 351, No. 22, pp. 2265-2275.

Shyu et al., Stromal Cell-Derived Factor-1alpha Promotes Neuroprotection, Angiogenesis, and Mobilization/Homing of Bone Marrow-Derived Cells in Stroke Rats, The Journal of Pharmacology and Experimental Therapeutics, 2008, vol. 324, No. 2, pp. 834-849.

Hau et al., Evidence for Neuroprotective Properties of Human Umbilical Cord Blood Cells After Neuronal Hypoxia in vitro, BMC Neuroscience, 2008, vol. 9, pp. 30-44.

Borlongan et al., Hibernation-Like State Induced by an Opioid Peptide Protects Against Experimental Stroke, BMC Biology, 2009, vol. 7, pp. 31-40.

Asahi et al., Reduction of Tissue Plasminogen Activator-Induced Hemorrhage and Brain Injury by Free Radical Spin Trapping After Embolic Focal Cerebral Ischemia in Rats, Journal of Cerebral Blood Flow and Metabolism, 2000, vol. 20, pp. 452-457.

Casalbore et al., Tumorigenic Potential of Olfactory Bulb-Derived Human Adult Neural Stem Cells Associates with Activation of TERT and NOTCH1, Plos One, 2009, vol. 4, No. 2, pp. E4434-E4443.

Chang et al., Regenerative Therapy for Stroke, Cell Transplantation, 2007, vol. 16, pp. 171-181.

Chen et al., Atorvastatin Induction of VEGF and BDNF Promotes Brain Plasticity After Stroke in Mice, Journal of Cerebral Blood Flow & Metabolism, 2005, vol. 25, pp. 281-290.

Cho et al., Lifetime Expression of Stem Cell Markers in the Uterine Endometrium, Fertility and Sterility, 2004, vol. 81, No. 2, pp. 403-407.

Chopp et al., Plasticity and Remodeling of Brain, Journal of Neurological Sciences, 2008, vol. 265, pp. 97-101.

De Coppi et al., Isolation of Amniotic Stem Cell Lines with Potential for Therapy, Nature Biotechnology, 2007, vol. 25, No. 1, pp. 100-106.

Delo et al., Amniotic Fluid and Placental Stem Cells, Methods in Enzymology, 2006, vol. 419, pp. 426-438.

Dimitrijevic et al., Effects of the Chemokine CCL2 on Blood-Brain Barrier Permeability During Ischemia-Reperfusion Injury, Journal of Cerebral Blood Flow & Metabolism, 2006, vol. 26, pp. 797-810.

Du et al., Contribution of Bone Marrow-Derived Stem Cells to Endometrium and Endometriosis, Stem Cells, 2007, vol. 25, pp. 2082-2086.

Flax et al., Engraftable Human Neural Stem Cells Respond to Developmental Cues, Replace Neurons, and Express Foreign Genes, Nature Biotechnology, 1998, vol. 16, pp. 1033-1039.

Garbuzova-Davis et al., Novel Cell Therapy Approaches for Brain Repair, Progress in Brain Research, 2006, vol. 157, pp. 207-222.

Haas et al., Adult Stem Cell Therapy in Stroke, Current Opinion in Neurology, 2005, vol. 18, pp. 59-64.

Hara et al., Transplantation of Post-Mitotic Human Neuroteratocarcinoma-Overexpressing Nurr1 Cells Provides Therapeutic Benefits in Experimental Stroke: In Vitro Evidence of Expedited Neuronal Differentiation and GDNF Secretion, Journal of Neuroscience Research, 2007, vol. 85, pp. 1240-1251.

Hara et al., Neural Progenitor NT2N Cell Lines from Teratocarcinoma for Transplantation Therapy in Stroke, Progress in Neurobiology, 2008, vol. 85, pp. 318-334.

Hess et al., Stem Cells and Neurological Diseases, Cell Proliferation, 2008, vol. 41, Suppl. 1, pp. 94-114.

Katakowski et al., Stroke-Induced Subventricular Zone Proliferation is Promoted by Tumor Necrosis Factor-alpha-Converting Enzyme Protease Activity, Journal of Cerebral Blood Flow & Metabolism, 2007, vol. 27, pp. 669-678.

Hida et al., Novel Cardiac Precursor-Like Cells from Human Menstrual Blood-Derived Mesenchymal Cells, Stem Cells, 2008, vol. 26, pp. 1695-1704.

Kishi et al., Variation in the Incidence of Teratomas After the Transplantation of Nonhuman Primate ES Cells Into Immunodeficient Mice, Cell Transplantation, 2008, vol. 17, pp. 1095-1102.

Lee et al., Human Neural Stem Cells Over-Expressing VEGF Provide Neuroprotection, Angiogenesis and Functional Recovery in Mouse Stroke Model, Plos One, 2007, vol. 2, No. 1, pp. E156-EE169.

Kondziolka et al., Stroke Repair with Cells Transplantation: Neuronal Cells, Neuroprogenitor Cells, and Stem Cells, Neurosurg. Focus, 2008, vol. 24, No. 3 & 4, pp. E12-E17.

Kurozumi et al., Mesenchymal Stem Cells That Produce Neurotrophic Factors Reduce Ischemic Damage in the Rat Middle Cerebral Artery Occlusion Model, Molecular Therapy, 2005, vol. 11, No. 1, pp. 96-104.

Matcham et al., GDNF in Parkinson's Disease: The Perils of Post-Hoc Power, Journal of Neuroscience Methods, 2007, vol. 163, pp. 193-196.

Matsukawa et al., Increased Expression of Hippocampal Cholinergic Neurostimulating Peptide-Related Components and Their Messenger RNAS in the Hippocampus of Aged Senescence-Accelerated Mice, Neuroscience, 1999, vol. 88, No. 1, pp. 79-92.

Meng et al., Endometrial Regenerative Cells: A Novel Stem Cell Population, Journal of Translational Medicine, 2007, vol. 5, pp. 57-66.

Nomura et al., I.V. Infusion of Brain-Derived Neurotrophic Factor Gene-Modified Human Mesenchymal Stem Cells Protects Against Injury in a Cerebral Ischemia Model in Adult Rat, Neuroscience, 2005, vol. 136, No. 1, pp. 161-169.

Ohab et al., A Neurovascular Niche for Neurogenesis After Stroke, The Journal of Neuroscience, 2006, vol. 26, No. 50, pp. 13007-13016.

Patel et al., Multipotent Menstrual Blood Stromal Stem Cells: Isolation, Characterization, and Differentiation, Cell Transplantation, 2008, vol. 17, pp. 303-311.

Schwab et al., Co-Expression of Two Perivascular Cell Markers Isolates Mesenchymal Stem-Like Cells from Human Endometrium, Human Reproduction, 2007, vol. 22, pp. 2903-2911.

(56) References Cited

OTHER PUBLICATIONS

Slevin et al., Unilateral Intraputamenal Glial Cell Line-Derived Neurotrophic Factor in Patients with Parkinson Disease: Response to 1 Year of Treatment and 1 Year of Withdrawal, J. Neurosurg., 2007, vol. 106, pp. 614-620.

Slevin et al., Leukaemia Inhibitory Factor is Over-Expressed by Ischemic Brain Tissue Concomitant with Reduced Plasma Expression Following Acute Stroke, European Journal of Neurology, 2008, vol. 15, pp. 29-37.

Paxinos et al., The Rat Brain in Stereotaxic Coordinates, Academic Press, 1998, San Diego.

Pisati et al., Induction of Neurotrophin Expression Via Human Adult Mesenchymal Stem Cells: Implication for Cell Therapy in Neurodegenerative Diseases, Cell Transplantation, 2007, vol. 16, pp. 41-55.

Prianishnikov, On the Concept of Stem Cell and a Model of Functional Morphological Structure of the Endometrium, Contraception, 1978, vol. 18, No. 3, pp. 213-223.

bdbiosciences.com; "CD117 (SCF R, c-kit)—BD Biosciences Catalog"; http://www.bdbiosciences.com/nvCategory.jsp?action=SELECT&form=formTree_catBean . . . ; Accessed on May 7, 2012.

ebioscience.com; "Mouse CD117 (c-kit) Antibody APC 2B8 RUO"; http://www.ebiosciences.com/mouse-cd117-c-kit-antibody-apc-2b8.htm.; Accessed on May 7, 2012.

leica-microsystems.com; "c-kit Oncoprotein (CD117)—Primary Antibodies: Leica Biosystems"; http://www.leica-microsystems.com/biosystems/products/total-histology/novocastra-reagent . . . Accessed on May 7, 2012.

miltenyibiotec.com; "CD117 MicroBead Kit (#130-091-332)"; http://www.miltenyibiotec.com/en/PG_625_350_CD117_MicroBead_Kit.aspx; Accessed on May 7, 2012.

Preliminary Amendment; U.S. Appl. 13/063,456, filed Mar. 10, 2011.

S. Thomas Carmichael, Rodent Models of Focal Stroke: Size, Mechanism, and Purpose. NeuroRX: The Journal of the American Society for Experimental NeuroTherapeutics. vol. 2, (2005) pp. 396-409.

Friedrich Gonner, et al., Local Intra-Arterial Thrombolysis in Acute Ischemic Stroke. Stroke: Journal of the American Heart Association. vol. 29, (1998) pp. 1894-1900.

Rui Lan Zhang, et al., A rat model of focal embolic cerebral ischemia. Brain Research, vol. 766, (1997) pp. 83-92.

\* cited by examiner

Experimental Outline

In Vitro Experiment:

- Culture of primary rat neurons

- Day 0: Co-culture with menstrual cells, exposed to conditioned media (harvested from cultured menstrual cells) or expose to control media

- Day 0: Oxygen deprivation to induce stroke in cultured cells

- Day 2: Assay cell survival and cell death

In Vivo Experiment:

- Pre operative behavioral baseline testing (8 animals/cohort)
- Day 0: Surgically induce stroke (MCA occlusion)
- Day 0: Transplantation immediately after stroke

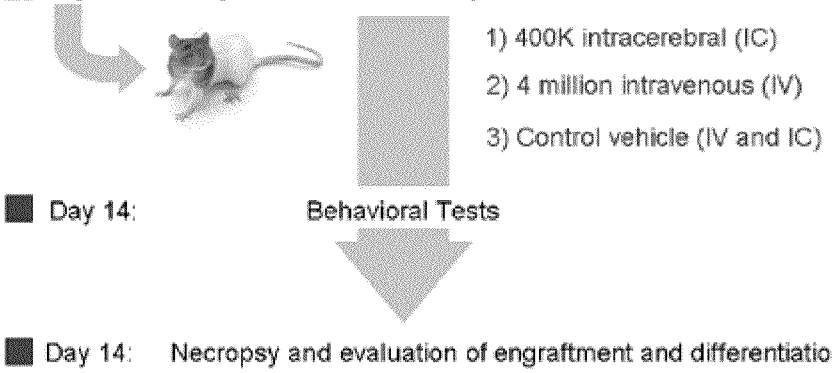

1) 400K intracerebral (IC)
2) 4 million intravenous (IV)
3) Control vehicle (IV and IC)

- Day 14: Behavioral Tests

- Day 14: Necropsy and evaluation of engraftment and differentiation

Schematic diagrams of in vitro and in vivo experimental procedures.
101x109mm (300 x 300 DPI)

Figure 3.

A    Oxygen glucose deprivation: cell death assay
Trypan Blue
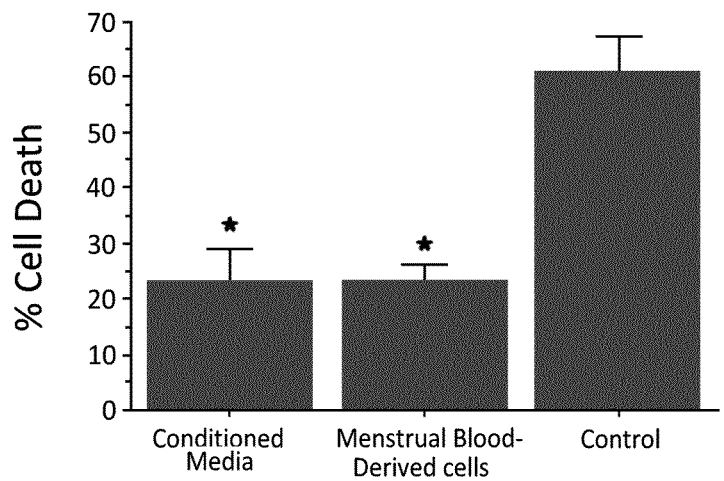
* Statisically significant, $p < 0.05$
B    Oxygen glucose deprivation: cell survival assay
MTT
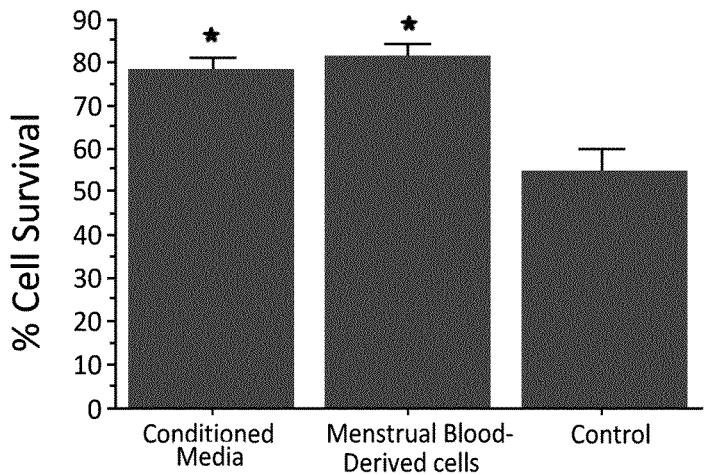
* Statisically significant, $p < 0.05$
Figure 4.

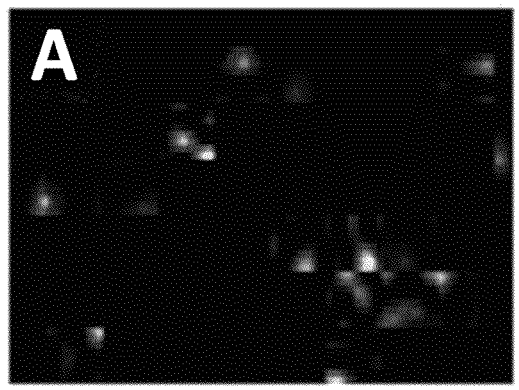
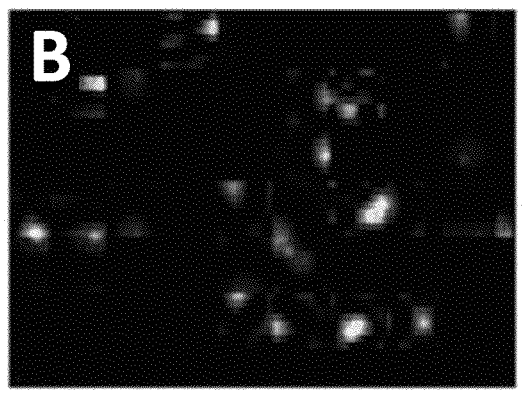
Figure 13.

METHODS OF TREATING STROKE USING STEM CELL-LIKE MENSTRUAL BLOOD CELLS

CROSS REFERENCE TO RELATED APPLICATION

This application is a continuation of International Application PCT/US2009/064379, entitled "Methods of Treating Stroke Using Stem Cell-Like Menstrual Blood Cells", filed on Nov. 13, 2009, which claims priority to U.S. Provisional Patent Application No. 61/114,311, entitled "Menstrual Blood Cells Display Stem Cell-like Phenotypic Markers and Exert Neuroprotection Following Transplantation in Experimental Stroke", filed on Nov. 13, 2008, the contents of which are herein incorporated by reference.

FIELD OF INVENTION

This invention relates to neurodegenerative and stroke therapy. Specifically, the invention is a method of treating stroke by administering a novel source of stem cell-like cells derived from menstrual blood.

BACKGROUND OF THE INVENTION

Stroke is the third leading cause of death and disability in adults in the US. Thrombolytic therapy only benefits about 2% of the ischemic stroke patients (Asahi, et al. (2000). Reduction of tissue plasminogen activator induced hemorrhage and brain injury by free radical spin trapping after embolic focal cerebral ischemia in rats. J Cereb Blood Flow Metab 20:452-457). The dismal record of neurorestorative regimens for stroke both in the laboratory and the clinic solicits an urgent need to develop novel therapies. Because the secondary cellular death that ensues after the initial stroke episode occurs over an extended time (Sicard, et al. (2006). Long-term changes of functional MRI-based brain function, behavioral status, and histopathology after transient focal cerebral ischemia in rats. Stroke 37:2593-2600; Virley, et al. (2000). A temporal MRI assessment of neuropathology after transient middle cerebral artery occlusion in the rat: correlations with behavior. J Cereb Blood Flow Metab 20:563-582; Wegener, et al. (2006). Temporal profile of T2-weighted MRI distinguishes between pannecrosis and selective neuronal death after transient focal cerebral ischemia in the rat. J Cereb Blood Flow Metab 26:38-47), treatment strategies directed at rescuing these ischemic neurons have the potential to retard the disease progression and even afford restoration of function (Borlongan C V. (2009). Cell therapy for stroke: remaining issues to address before embarking on clinical trials. Stroke 40(3 Suppl):S146-148; Stem Cell Therapies as an Emerging Paradigm in Stroke Participants. (2009). Stem Cell Therapies as an Emerging Paradigm in Stroke (STEPS): bridging basic and clinical science for cellular and neurogenic factor therapy in treating stroke. Stroke 40:510-515). The recognition of this delay in secondary stroke-induced pathophysiologic alterations has prompted investigations on neurorestorative treatments, including cell therapy, to salvage the ischemic penumbra and promote functional recovery from stroke. Cell therapy thus offers a new avenue for the treatment and management of stroke.

The transplantation of adult stem cells derived from bone marrow has been successfully used in treatment of human disease, such as Fanconi's Anemia, aplastic anemia, acute and chronic leukemias, myeloproliferative disorders, myelodysplatic syndromes, lymphoproliferative disorders, and other malignancies. Alternative sources of bone marrow adult stem cells include peripheral blood progenitor cells, umbilical cord blood and mesenchymal stem cells harvested from these sources. However, there are several shortcomings associated with therapeutic use of adult stem cells. Adult stem cells have been shown to have limited efficacy, such as slow growth and loss of pluripotency after several passages in culture.

Embryonic stem (ES) cells are pluripotent cells that can differentiate to all specialized cell types of the organism (Vescovi & Snyder (1999). Establishment and properties of neural stem cell clones: plasticity in vitro and in vivo. Brain Pathol 9:569-598. Review; Flax, et al. (1998). Engraftable human neural stem cells respond to developmental cues, replace neurons, and express foreign genes. Nat Biotechnol 16:1033-1039). Unfortunately, numerous ethical and logistical considerations limit the utility of these cells, which can only be isolated from the inner cell mass of early embryos. Moreover, the tumorigenicity of ES cells remains a major obstacle for clinical application (Casalbore, et al. (2009). Tumorigenic potential of olfactory bulb derived human adult neural stem cells associates with activation of TERT and NOTCH1. PLoS ONE 36 [PubMed—in process]; Kishi, et al. (2008). Variation in the incidence of teratomas after the transplantation of nonhuman primate ES cells into immunodeficient mice. Cell Transplant 17:1095-1102.). The advent of adult stem cells circumvents the inherent problems of ES cells. Although the multipotent property of adult stem cells has been debated, accumulating evidence indicates these cells possess embryonic stem cell-like features including their ability to differentiate into tissues of an entirely different germ layer (Hess & Borlongan (2008). Stem cells and neurological diseases. Cell Prolif 41:94-114; Haas, et al. (2005). Adult stem cell therapy in stroke. Curr Opin Neurol 18:59-64. Review; Chang, et al. (2007). Regenerative therapy for stroke. Cell Transplant 16:171-181; Chopp, et al. (2008). Plasticity and remodeling of brain. J Neurol Sci 265:97-101; Bliss, et al. (2007). Cell transplantation therapy for stroke. Stroke 38:817-826; Kondziolka & Wechsler (2008). Stroke repair with cell transplantation: neuronal cells, neuroprogenitor cells, and stem cells. Neurosurg Focus 24:E13; Garbuzova-Davis, et al. (2006). Novel cell therapy approaches for brain repair. Prog Brain Res 157:207-222).

Effects of the human immune system, the body's inherent mechanism to defend itself from infection and foreign substances, became a critical consideration in early transplants as researchers' encountered illness and/or fatalities resulting from the body's rejection of rejection of cells later characterized as Graft versus Host Disease (GVHD). The bone marrow and umbilical cord blood are the two most studied adult stem cells, and have been proposed for autologous transplantation. The availability of a transplant donor cell type that completely matches the transplant recipient appears as an optimal scenario for cell therapy in view of graft-versus-host complications, in the event of a mismatch between donor and recipient, largely resulting in transplant failure in hematopoietic stem cell transplantation (Remberger, et al. (2007). Major ABO blood group mismatch increases the risk for graft failure after unrelated donor hematopoietic stem cell transplantation. Biol Blood Marrow Transplant 13:675-682; Fleischhauer, et al. (2006). Graft rejection after unrelated donor hematopoietic stem cell transplantation for thalassemia is associated with nonpermissive HLA-DPB1 disparity in host-versus-graft direction. Blood 107:2984-2992). Of interest, immature donor cell sources, such as umbilical cord blood, seem to be relatively tolerated by the transplant recipient despite a HLA mismatch (Laughlin, et al. (2004). Outcomes after transplantation of cord blood or bone marrow from unrelated donors in adults with leukemia. N Engl J Med 351:2265-2275). Accordingly, strategies designed to amplify autologous transplantation should benefit a large patient population. The derivation of adult stem cells from the bone marrow may be painful, whereas harvesting umbilical cord blood is, of course, limited during the baby delivery.

Cell therapy remains an experimental treatment for neurological disorders. The number of cells required for transplant therapies then to be large, whereas only a small, limited number of umbilical cord blood cells can be collected, requiring the umbilical cord blood cells to be expanded prior to use. A major obstacle in pursuing the clinical application of this therapy is finding the optimal cell type that will allow benefit to a large patient population with minimal complications. A cell type that is a complete match of the transplant recipient appears as an optimal scenario. Indeed, the use of autologous bone marrow or umbilical cord blood has been proposed as a good source of stem cells for cell therapy. However, there can be difficulties in promulgating umbilical cord blood cell cultures. Some solutions to these problems include co-culturing umbilical cord blood cells with menstrual blood cells, as described in Walton, et al. (U.S. application Ser. No. 12/290,551).

SUMMARY OF THE INVENTION

The remarkable capacity of the uterine lining to regenerate after each menstrual cycle has been noted (Prianishnikov (1978). On the concept of stem cell and a model of functional morphological structure of the endometrium. Contraception 18:213-223). Menstrual blood is shown to be another important source of stem cells (Patel, et al. (2008). Multipotent Menstrual Blood Stromal Stem Cells: Isolation, characterization and differentiation. Cell Transplant 17:303-311). Extraction of this rich source of stromal cells is efficient and non-controversial. In studying the cells released from the uterine lining as part of the menstrual blood, multipotent cells capable of differentiating into chrondrogenic, adipogenic, osteogenic, neurogenic, endothelial, pulmonary epithelial, hepatic/pancreatic and cardiogenic cell lineages have been identified and characterized (Meng, et al. (2007). Endometrial regenerative cells: a novel stem cell population. J Transl Med 15; 5:57). Immunocytochemical assays of cultured menstrual blood reveal that they express embryonic like-stem cell phenotypic markers (Oct4, SSEA, Nanog), and maintain potency to differentiate and display highly proliferative capabilities. When grown in appropriate conditioned media, the cells express neuronal phenotypic markers (Nestin, MAP2). Menstrual blood-derived stem cells thus pose as a novel cell population that may be routinely and safely isolated and provide a renewable source of stem cells from child-bearing women.

Neural stem cell features were characterized and their potential as graft source for stroke therapy and method of treating ischemia comprising administering a therapeutically effective amount of an isolated menstrual blood-derived stem cell enriched cell population is evaluated. Optionally, the menstrual blood-derived stem cell enriched cell population are cultured prior to administrating the cells, such as culturing in neural induction medium and retinoic acid. The medium may optionally include DMEM/F12 supplemented with N2 and FGF-2. The menstrual blood-derived stem cell enriched cell population may be treated with a plurality of antibiotics prior to administration and/or filtered with a 100 μm filter. The isolated menstrual blood-derived stem cell enriched cell population may be administered within 2 hours of stroke. The cells maintain potency to differentiate and display highly proliferative capabilities which may be linked to embryonic stem cell surface markers retained on the cells (i.e. SSEA-4, Oct-4). Menstrual blood-derived stem cells thus pose as a novel cell population that may be routinely and safely isolated and provide a renewable source of stem cells from child-bearing women.

In some embodiments, the isolated menstrual blood-derived stem cell population is selected for CD 117 and/or for adherent cells. The menstrual blood-derived stem cell enriched cell population also is optionally selected based on excreted trophic factors, specifically for vascular endothelial growth factor, brain-derived neurotrophic factor, and/or neurotrophin-3. The isolated menstrual blood-derived stem cell population may be administered intravenously or intracranially, such as implanted 0.5 mm anterior to the bregma, 2.8 mm lateral to midline, and 5.0 mm below the dural surface or administered into the jugular vein. In specific embodiments of the invention, the isolated menstrual blood-derived stem cell enriched cell population is administered at between $4 \times 10^5$ cells and $4 \times 10^6$ cells. Transplantation of menstrual blood-derived stem cells, either intracerebrally or intravenously, after experimentally induced ischemic stroke in adult rats significantly reduced behavioral and histological impairments compared to vehicle-infused rats.

A method of treatment of ischemia using trophic factors from a population of menstrual blood-derived stem cells is also disclosed. The menstrual blood-derived stem cells are isolated from menstrual blood and incubated, such that the population of menstrual blood-derived stem cells excrete at least one of vascular endothelial growth factor, brain-derived neurotrophic factor, and neurotrophin-3. The trophic factors are collected and administered into the patient. In some embodiments of the invention, the human menstrual blood-derived stem cell population is cultured in DMEM/F12 supplemented with N2 and FGF-2.

BRIEF DESCRIPTION OF THE DRAWINGS

For a fuller understanding of the invention, reference should be made to the following detailed description, taken in connection with the accompanying drawings, in which:

FIG. 3 is a schematic diagram showing an outline of the in vitro and in vivo experimental procedures.

FIGS. 4(a)-(b) are graphs showing co-cultured menstrual blood-derived stem cells protects against in vitro stroke insult. Cell viability tests using (A) Trypan blue exclusion method and (B) MTT assay revealed that OGD exposed primary rat neurons that were co-cultured with menstrual blood-derived stem cells or exposed to the media collected from cultured menstrual blood-derived stem cells exhibited significantly protected against ischemic cell death, with no significant differences in the protection afforded. Error bars represent standard deviations. Data were generated from two triplicates of two different menstrual blood-derived stem cell samples. Asterisk * corresponds to statistically significant difference between conditioned media or menstrual blood-derived stem cells and control.

FIGS. 13(a)-(b) are images showing control brains in the menstrual blood-derived stem cells transplant experiments (seen in FIGS. 9-12). Brains from a stroke animal that received IC vehicle, demonstrating absence of (A) HuNu and (B) Oct4 labeling, respectively. Scale bar=10 μm.

DETAILED DESCRIPTION OF THE PREFERRED EMBODIMENT

Figure 1:
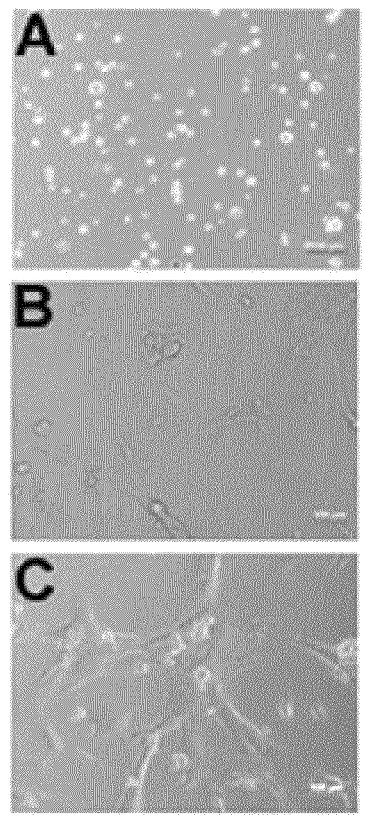
FIGS. 1(a)-(c) are images of cultured menstrual blood cells can be steered towards neural lineage. Morphological changes in cultured menstrual blood cells immediately following thawing (A), after a few hours (B) and prolonged exposure (C) in neural induction medium (DMEM/F12 supplemented with N2 and FGF-2).
Figure 2:
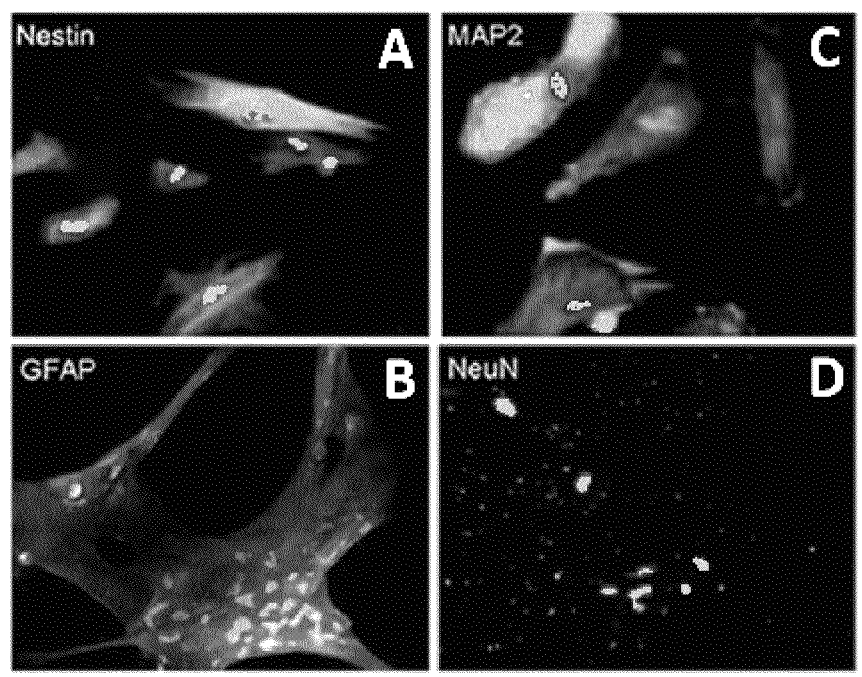
FIGS. 2(a)-(d) are images of cultured menstrual blood cells can be steered towards neural lineage. After passage 6 or 9, the cells were transferred to coated dishes in neural induction medium for a week, then retinoic acid was added to the medium over the next 3 weeks. Cells were stained for (A) Nestin positive, indicative of an early neural lineage commitment, which readily differentiated into (B) MAP2 positive cells (30%) showing an intermediate neuronal phenotype; (C) GFAP positive cells (40%) showing astrocytic phenotype upon withdrawal of FGF-2; and (D) staining for NeuN, but the mature neuronal marker. Thus, when grown in appropriate conditioned media, cultured menstrual blood stem cells express neural phenotypic markers (Nestin, MAP2).
Figure 5:
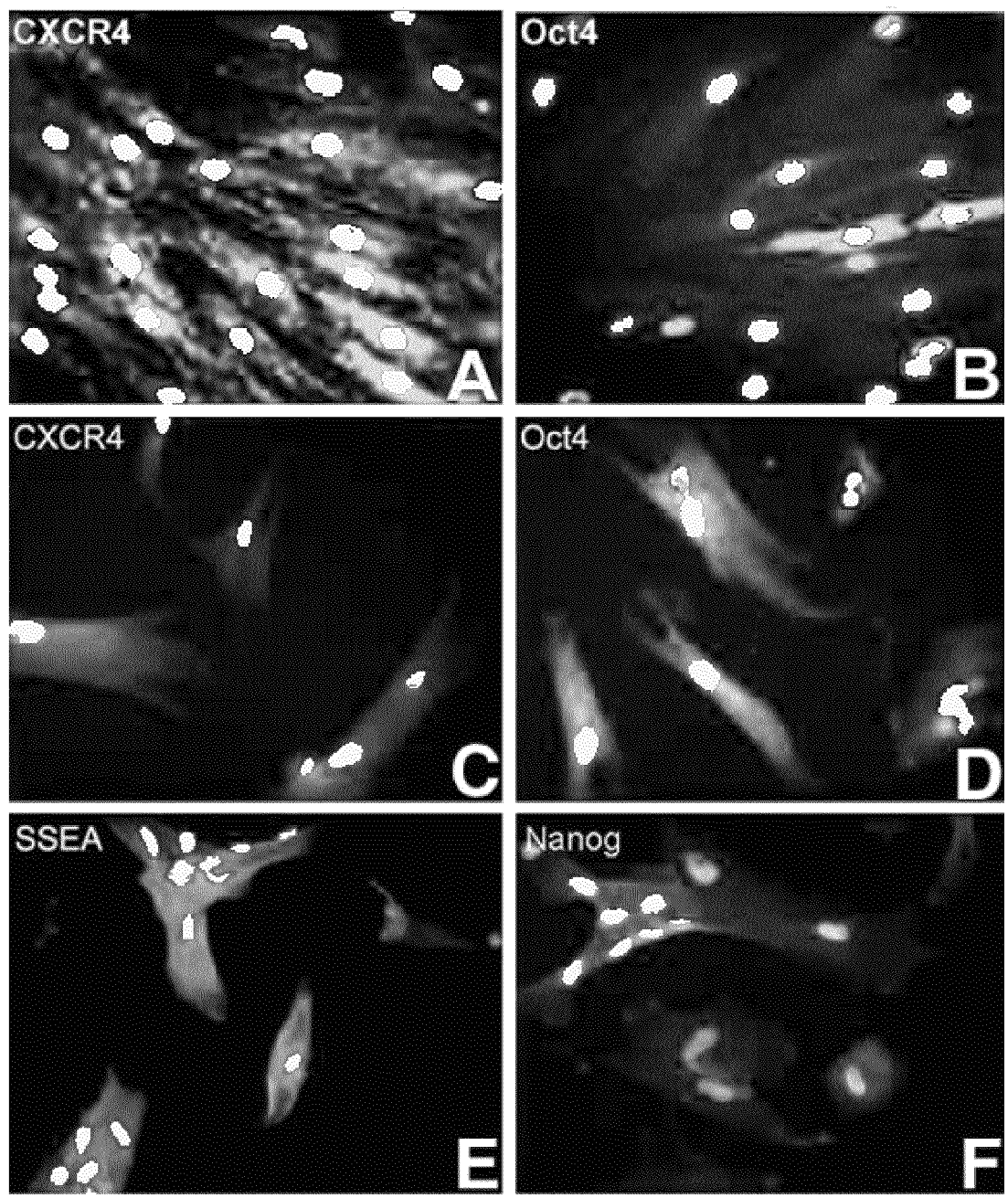
FIGS. 5(a)-(f) are images showing cultured menstrual blood cells display embryonic stem cell-like features. (A) and (B) are positive control images taken from human embryonic stem cells expressing the phenotypic markers Oct4 and CXCR4. Immunocytochemical assays of cultured menstrual blood reveal that these cells (75%) were (C) CXCR4 positive, a stem cell chemotaxis marker. Furthermore, they express embryonic like-stem cell phenotypic markers (D) Oct4, (E) SSEA, and (F) Nanog as shown. Greater than 90% of the cells were positive for these pluripotent markers. They maintained these stem-like properties at least up to passage 9 plus the additional 3 passages in culture (i.e., longest time point the cells were cultured in this study). In addition, their growth rate or proliferative capacity did not change over time. The cells were plated on a coated 10-cm dish in DMEM/F12 supplemented with ITS and medium was changed twice a week throughout the study.

The term "menstrual cell" refers to cells collected from menstrual flow according to any of the methods of Walton, et al. (U.S. application Ser. No. 12/074,423). The menstrual cells comprises cells expressing at least one of the cell markers or intracellular markers including, but not limited to CD 9, CD 10, CD 13, CD 29, CD 41a, CD 44, CD 49e, CD49f, CD 59, CD 73, CD 81, CD 90, CD 105, CD 166, and HLA class I, while expressing low or no levels of CD 3, CD 14, CD 31, CD 33, CD 34, CD 133, MHC II., and the pan-leukocyte marker CD45. While "cell" is used in the singular sense, it is envisioned that the invention may also use a plurality of cells. Accordingly, "cell" or "cells" may be used interchangeable in either the singular or plural sense of the word. While the characteristics described above are provided as exemplary characteristics, additional and alternative cell surface are provided through the disclosure of the invention, including without limiting the invention, the characteristics provided on any table and/or figure, the disclosure regarding the menstrual stem cells of the present invention, and throughout the disclosure of Walton, et al. (U.S. application Ser. No. 12/074,423) and Walton, et al. (U.S. application Ser. No. 12/290,551). In specific examples, the menstrual blood cells are pluripotent or omnipotent, such that the cells show potential to differentiate into various cell lineages, such as neural, cardiogenic, chondrogenic, adipogenic, and osteogenic cell lineages.

The term "ischemia" and "stroke" broadly refers to local tissue anemia due to the reduction or cessation of blood flow to the central nervous system, regardless of whether such cessation is a result of a systemic circulatory failure, such as those cause by shock, cardiac failure, or cardiac arrest or from a partial or complete occlusion in the intracranial or extracranial cerebral arteries.

The term "effective amount" or pharmaceutically effective amount" refers to a nontoxic, but significant, amount of the disclosed composition required to provide the desired biological result. The result can be a reduction and/or alleviation of symptoms, causes of disease, or other desired alteration of a biological system. Other intended results may include, without limiting the scope of the invention, differentiating stem and/or progenitor cells into specialized cells, such as neural, neuronal and/or glial cells, or treating a neurological disorder or other pathologic condition including damage to the central nervous system of a patient, such as a stroke, heart attack, or accident victim or for effecting a transplantation of those cells within the patient to be treated. An "effective amount" for therapeutic purposes is the amount of the composition of menstrual blood stem cells required to provide a clinically significant decrease in stroke, infarct, and other neurodegenerative and neurodamaging diseases resulting from inflammatory or ischemic conditions in the brain. Compositions according to the present invention may be used to effect a transplantation of menstrual blood-derived stem cell-like cells to produce a favorable change in the brain or spinal cord, or in the disease or condition treated, whether that change is an improvement such as stopping or reversing the degeneration of a disease or condition, reducing a neurological deficit or improving a neurological response, or a complete cure of the disease or condition treated. An appropriate effective amount may be determined by one of ordinary skill in the art using routine experimentation.

The terms "grafting" and "transplanting" and "graft" and "transplantation" are used throughout the specification synonymously to describe the process by which cells of the subject invention are delivered to the site where the cells are intended to exhibit a favorable effect, such as repairing damage to a patient's central nervous system (which can reduce a cognitive or behavioral deficit caused by the damage), treating a neurodegenerative disease or treating the effects of nerve damage caused by stroke, cardiovascular disease, a heart attack or physical injury or trauma or genetic damage or environmental insult to the brain and/or spinal cord, caused by, for example, an accident or other activity. Cells of the subject invention can also be delivered in a remote area of the body by any mode of administration as described above, relying on cellular migration to the appropriate area to effect transplantation. Preferably the cells are administered with a blood brain barrier permeabilizer.

The term "treat" or "treatment" means repairing damage to a patient's central nervous system and/or a reduction in clinically significant decreases in stroke, infarct, and other neurodamaging diseases resulting from inflammatory or ischemic conditions in the brain and/or reduction in the severity of symptoms that have or are expected to develop. The term also is intended to include favorable changes in the brain or spinal cord, or in the disease or condition treated, regardless of whether that change is an improvement such as stopping or reversing the degeneration of a disease or condition, or a complete cure of the disease or condition treated.

The term "patient" includes mammals and non-mammals. Non-limiting examples include humans, non-human primates, species of the family bovidae, species of the family suidae, domestic animals including rabbits, dogs, and cats, laboratory animals, such as rats, mice, guinea pigs, and non-mammals, including birds and fish.

In general, the compounds of the present invention are administered in a therapeutically effective amount by any accepted mode of administration. Suitable dosage ranges depend upon factors known to one skilled in the art. Non-limiting examples of factors include the severity of the disease to be treated, the age of the patient, the relative health of the subject, the potency of the compound utilized, and the route and form of administration. Once of skill in the art will also be capable of ascertaining the therapeutically effective amount of compound needed for a given disease, without undue experimentation and in reliance of his or her experience.

Compounds of this invention are administered as pharmaceutical formulations, including those suitable for pulmonary or parenteral-including intramuscular, intraarterial, intrathecal, subcutaneous, and intravenous. In some embodiments, intravenous or intraarterial administration is a preferred manner of providing a daily dosing regimen that can be adjusted according to the degree of affliction.

Parenteral formulations may be prepared using conventional materials, either as liquid solutions or suspensions, solid forms suitable for use in suspension or solublization before injection, or emulsion. Injectable solutions or suspensions using known dispersing or wetting agents are known in the art, and optionally include nontoxic diluents or solvents. Exemplary vehicles include, without limiting the scope of the invention, water, Ringer's solution, isotonic sodium chloride, and phosphate buffered saline. Sterile, fixed oils, fatty esters, and polyols. The parenteral solution or solvent may also include a slow release or sustained release systems, which maintains a constant dosage level.

Standard molecular biology techniques known in the art and not specifically described are generally followed as in Sambrook et al., Molecular Cloning: A Laboratory Manual, Cold Springs Harbor Laboratory, New York (1989, 1992), and in Ausubel et al., Current Protocols in Molecular Biology, John Wiley and Sons, Baltimore, Md. (1989).

Menstrual flow may be collected with any known collection process, such as the process described in Walton, et al. (U.S. application Ser. No. 12/074,423), and transferred to a facility where the menstrual flow may be processed to isolate and collect stem cells. The isolation and collection of menstrual blood stem cells from the menstrual flow may occur by way of centrifugation, density gradient centrifugation, filtration or sedimentation methodologies used to maximize the number of menstrual blood stem cells collected. Once collected, the menstrual blood stem cells may be further processed and/or cryopreserved as known in the art. Methods of preparing menstrual blood stem cells for cryopreservation, and methods of cryopreserving said stem cells is recognized in the art, as evidenced by Walton, et al. (U.S. application Ser. No. 12/074,423). Cryopreserved menstrual blood stem cells may be thawed at a later point for processing and/or use.

The menstrual blood cells were collected via a procurement kit prepared by the processing facility approved under an IRB study for the collection, processing, cryopreservation and post thaw viability of the harvested cells (Patel, et al. (2008). Multipotent Menstrual Blood Stromal Stem Cells: Isolation, characterization and differentiation. Cell Transplant 17:303-311). The menstrual blood procurement kit included a transport container prepared with a Styrofoam box suitable for shipping cells at a cool temperature. A collection device called a menstrual collection cup was commercially available to harvest the cells during the participant's menstrual cycle. A sterile container for transport included a 50 ml container; Dulbecco's Phosphate Buffer Saline (DPBS) (Mediatech or equivalent including other media) that contains no calcium, magnesium or phenol red; antibiotics included Penicillin (100 units per milliliter) and Streptomycin (100 micrograms per milliliter) and Amphotericin B (2.5 micrograms per milliliter); Heparin preservative-free which was used at a concentration of 10 units per milliliter of the media; an antiseptic wipe used prior to insertion of cup and before removal of cup for sample collection. Menstrual blood was collected and transferred to a sterile container by aseptically transferring the sample for shipment, as described in Walton, et al. (U.S. applicatiopn Ser. No. 12/074,423). Collections took place over 4 hours or less. Menstrual blood was collected on day 1, 2 or 3 during the heaviest flow of the cycle. On an average 8-10 mls were collected per sample, with approximately 30 million cells and from 0.5 to 40% of adherent cells. All samples collected were stored between 1° C. and 10° C., typically at 4° C., post collection. The samples were shipped to the laboratory on frozen bricks to assure shipment of cells at a cool temperature.

Menstrual blood was processed and stem cells collected as described in Walton, et al. (U.S. application Ser. No. 12/074, 423). Briefly, a buffered saline media (DPBS) is used throughout the cell isolation process with Heparin (Heparin Sodium 1,000 USP Units/ml—American Pharmaceutical Partners, Schaumburg, Ill.). The menstrual cells collected in a buffered saline conical collection tube were subjected to centrifugation at 840×g for seven (7) minutes between 1° C. to 10° C. The supernatant was used for microbiological testing. Pelleted cells were resuspended for a cell count and viability. The cells were prepared for cryopreservation. Bacteriological analysis of the supernatant was performed using the BacT/ALERT system (Biomerieux, Durham, N.C.). The cells were grown to either passage 6 or 9 and cultured for additional 3 passages before testing without observing signs of contamination. Most products tested had some level of contamination but after a treatment of an antibiotic cocktail, when the cells were thawed post processing, the culture was found negative of contaminants. One ml of cellular suspension was tested for the total cell count, cell viability and flow cytometric analysis for specific markers. The entire sample was filtered with a 100 micron filter prior to cryopreserving the cells. One ml of cellular suspension was tested for the total cell count, cell viability and flow cytometric analysis for specific markers.

The cells were then cryopreserved in a total volume of 10 ml comprising of five ml of cells, three ml of the buffered saline (DPBS), one (1) ml of the protein HSA (Telacris Bio, Clayton, N.C.), and one (1) ml of the preservative DMSO (99% Stemsol). Cells were stored in five (5) ml bar-coded cryovials included cap storage for a QC sample (Nalgene, Roskilde, Denmark). Cells were cryopreserved in a controlled rate freezer beginning at 4° C. reducing the temperature by approximately 1° C./minute until it reached –90° C. (Controlled Rate Freezer 7454—Thermo Electron, Corp. Marietta, Ohio). When the sample reached –90° C., the cryovials were transferred to a cryogenic storage unit and stored in the vapor phase of liquid Nitrogen at a temperature at or below –150° C. (LN2 Freezer MVE 1830—Chart Industries, Garfield Heights, Ohio).

Cells were thawed to expand in culture and selected for CD117 (Patel, et al. (2008). Multipotent Menstrual Blood Stromal Stem Cells: Isolation, characterization and differentiation. Cell Transplant 17:303-311). The freeze thaw process demonstrated a high level of viability after adherent cells had been selected for CD117. Most passages revealed close to 100% viability as determined by 7-AAD. CD117 selection was performed via Miltenyi system at post thaw, with positive selected cells subsequently expanded in culture. CD117 has been previously identified in endometrial cells, and shown to be closely associated with a highly proliferative cell type and appears to promote cell survival and migration (Cho, et al. (2004). Lifetime expression of stem cell markers in the uterine endometrium. Fertil Steril 81:403-407). Briefly, to thaw cells they were agitated in a 37° C. water bath, transferred to chilled Chang's complete media (Chang & Jones (1982). A new growth medium for human amniotic fluid cells. Proc Natl. Acad. Sci. USA 79:4795; 148; Delo, et al. (2006). Amniotic fluid and placental stem cells. Methods Enzymology 419:426-438) with DNase (10 drops per 100 mL). For a 5 mL cell preparation, 25 mL of chilled media was used. Cells were washed in the centrifuge at 120 g for 5 minutes and re-suspended in Chang's complete media without DNase by gentle inversion. Only 1 million cells are required for the first cell culture to select the adherent cells with generally about 10% of the cells demonstrating adherence and about 100,000 cells subcultured. The cells were observed to double approximately every 24 hours. As such, cells were seeded in T-25 non-treated tissue culture flask with approximately 1 million cells/flask. The leukocytes were not removed from the cell preparation, but only the adherent cells remained in culture and the adherent layer was subcultured to expand the cells. Once cells were subcultured they were seeded at $2000/cm^2$ and plated in a T-25 flask included 7 mL of Chang's complete media. Cells were incubated in a 5% $CO_2$ incubator at 36.0-38.0° C. until they are confluent to 70-80%. When cells were subcultured the flask was rinsed with 5 ml DPBS and then treated with 1.5 ml of pre-warmed TrypLE (Invitrogen #12605-010; location Carlsbad, Calif.) incubated at 36.0-38.0° C. After incubation cells were dislodged by gently tapping the flask contents, the cells were then diluted and transferred to a tube for centrifugation. Cells were seeded to expand and when there was a minimum of 2.5 million total nucleated cells they were selected for CD117. The CD117 stem cells were separated from a cellular suspension in working buffer using a MS column and MiniMACS kit (Miltenyi Biotec, Bergisch Gladbach, Germany) which include microbeads was used for CD117 cell selection. The MS column was prepared by rinsing it with working buffer (500 µl). The column was placed in the magnetic field of a MACS separator available through Miltenyi Biotec to retain the positive fraction prior to collection of the fraction. Collected cells were subcultured and expanded for functional studies.

After passage 6 or 9, the cells were transferred to coated dishes in neural induction medium (DMEM/F12 supplemented with N2 and FGF-2) for a week, then retinoic acid was added to the medium over the next 3-4 weeks. Cells were Nestin positive, indicative of an early neural lineage commitment, and readily differentiated into intermediate neuronal (30% MAP2 positive, but the mature neuronal marker, NeuN, labeling not detected) and astrocytic phenotype (40% GFAP positive) upon withdrawal of FGF-2, as seen in FIGS. 1(a)-(c) and 2(a)-(d). Thus, when grown in appropriate conditioned media, cultured menstrual blood stem cells express neural phenotypic markers (Nestin, MAP2).

Aliquots derived from the two samples of cells, either passaged 6 and 9 then grown for additional 3 passages in culture, were found to behave similarly, with cell yields, number of adherent cells and those expressing neuronal phenotypes, as well as graft survival and functional effects showing near complete resemblance of the two cell populations. Thus, the data from these two cell populations were collapsed into a single treatment condition. A flow chart of experimental procedures is shown in FIG. 3.

EXAMPLE 1

In Vitro Use of Menstrual Blood Stem Cells in Stroke Models

Primary cultures of neurons were derived from the rat (Sprague-Dawley) striatum and maintained in culture following the supplier's protocol (CAMBREX, MD). Briefly, immediately after thawing, cells ($4 \times 10^4$ cells/well) were seeded and grown in 96-well plate coated by poly-1 lysine in Neurobasal media (GIBCO, CA) containing 2 mM L-glutamine, 2% B27 (GIBCO, CA) and 50 U/ml penicillin and streptomycin for 7-10 days at 37° C. in humidified atmosphere containing 5% $CO_2$. Purity of the cells were immunocytochemically determined to be >99% for neuronal cell population as revealed by DARPP-32 immunostaining. Moreover, these cells were appropriate for the oxygen glucose deprivation (OGD) injury model, where glutamate excitotoxicity plays an important role, as revealed by expression of glutamate receptors (determined immunocytochemically using vesicular glutamate transporter-1) in 50% of the neuronal and astrocytic cell population.

Cultured cells were exposed to the oxygen-glucose deprivation (OGD) injury model as described previously (Malagelada, et al. (2004) Histamine H2-receptor antagonist ranitidine protects against neural death induced by oxygen-glucose deprivation. Stroke 35: 2396-2401) with few modifications. Briefly, cultured CD117+ cells at passage 6 and 9 were cultured for an additional 3 passages and the culture medium replaced by a glucose-free Earle's balanced salt solution (BSS) with the following composition (116 mM NaCl, 5.4 mM KCl, 0.8 mM $MgSO_4$, 1 mM $NaH_2PO_4$, 26.2 mM $NaHCO_3$, 0.01 mM glycine, 1.8 mM $CaCl_2$), and pH adjusted to 7.4 with or without minocycline). Cultured cells were placed in humidified chamber, and then equilibrated with continuous flow of 92% $N_2$ and 8% $O_2$ gas for 15 minutes. After this equilibrium, the chamber was sealed and placed into the incubator at 37° C. for 48 hours for MTT assay and Trypan blue stain.

Cell viability was evaluated by ATP activity following the supplier's protocol (Promega, WI) and by Trypan blue (Sigma, MO). Briefly, the chemiluminescence-based MTT assay was carried out by adding MTT assay solution immediately after OGD. Spectrometric absorbance measured at 595 nm (for formazan dye) and with the absorbance at >650 nm for reference. The intensities of chemiluminescence of ATP activity were measured and calculated by Image station 2000R system (Kodak, NY). In addition, Trypan blue exclusion method was conducted and mean viable cell counts were calculated in three randomly selected areas (0.2 $mm^2$) in each well (n=5 per treatment condition) to reveal the cell viability for each treatment condition. ANOVA revealed significant treatment effects in both Trypan blue exclusion method ($F_{2,6}$=58.78, $p<0.0001$) and MTT assay ($F_{2,6}$=45.60, $p<0.001$) for detecting cell death and cell survival, respectively. Posthoc tests revealed that menstrual blood-derived stem cells (Trypan blue exclusion method and MTT assay, p's<0.0001 vs. controls) or the media collected from cultured menstrual blood-derived stem cells (Trypan blue exclusion method, $p<0.0001$ vs. controls; MTT assay, $p<0.001$ vs. controls) significantly reduced cell death and improved cell survival of OGD-exposed primary neurons. The in vitro oxygen glucose deprivation (OGD) stroke model showed that OGD-exposed primary rat neurons that were co-cultured with menstrual blood-derived stem cells or exposed to the media collected from cultured menstrual blood-derived stem cells exhibited significantly protected against ischemic cell death.

In order to test the therapeutic potential of these cells, in vitro oxygen glucose deprivation (OGD) stroke model was used. OGD-exposed primary rat neurons that were co-cultured with menstrual blood-derived stem cells or exposed to the media collected from cultured menstrual blood-derived stem cells exhibited significantly protected against ischemic cell death, as seen in FIGS. 4(a) and (b). ANOVA revealed significant treatment effects in both Trypan blue exclusion method ($F_{2,6}$=58.78, $p<0.0001$), shown in FIG. 4(a), and MTT assay ($F_{2,6}$=45.60, $p<0.001$), shown in FIG. 4(b), for detecting cell death and cell survival, respectively. Posthoc tests revealed that menstrual blood-derived stem cells (Trypan blue exclusion method and MTT assay, p's<0.0001 vs. controls) or the media collected from cultured menstrual blood-derived stem cells (Trypan blue exclusion method, $p<0.0001$ vs. controls; MTT assay, $p<0.001$ vs. controls) significantly reduced cell death and improved cell survival of OGD-exposed primary neurons. There were no significant differences in the protective effects afforded by co-culturing with menstrual blood-derived stem cells and exposure to the media collected from cultured menstrual blood-derived stem cells (p's>0.1).

Cultures were prepared for immunocytochemical assay. The cells were plated on a coated 10-cm dish in DMEM/F12 supplemented with ITS and medium was changed twice a week throughout the study. Each $1 \times 10^5$ cells were plated on 8 well Permanox® slides (Nalge Nunc Int, IL) two days before fixation. Cultured cells were treated with 4% paraformaldehyde (PFA) for 10 minutes at room temperature after rinsing with phosphate buffered saline (PBS). After blocking reaction with 10% normal goat serum (Vector, CA), cells were incubated overnight at 4° C. with specific antibodies against Oct4 (1:1000, Abcam, MA, USA), SSEA (1:200, Abcam, MA, USA), Nanog (1:500, Abcam, MA, USA), CXCR4 (1:100, Abcam, MA, USA), Nestin (1:200, Abcam, MA, USA), MAP2 (1:1000, Abcam, MA, USA), GFAP (1:100, Abcam, MA, USA) and NeuN (1:1000, Abcam, MA, USA) with 10% normal goat serum. After several rinses in PBS, cells were incubated for 45 minutes at room temperature in FITC-conjugated anti-mouse IgG (1:1000, Molecular probe, CA), or Rhodamine-conjugated anti-rabbit IgG (1:2000, Molecular probe, CA) for visualization. Cells were processed for DAPI immunostaining then subsequently embedded with mounting medium. Immunofluorescent images were visualized using Zeiss Axiophot 2. In addition, control studies included exclusion of primary antibody and substituted with 10% normal goat serum in PBS. No immunoreactivity was observed in these controls. All studies were conducted in triplicates. Assessment was performed blindly by an independent investigator.

Immunocytochemical assays of cultured menstrual blood reveal that they express embryonic like-stem cell phenotypic markers (Oct4, SSEA, Nanog), seen in FIGS. 5(a)-(f). Greater than 90% of the cells were positive for these pluripotent markers. They maintained the stem-like properties at least up to 3 passages (i.e., longest time point the cells were cultured in this study). In addition, their growth rate or proliferative capacity did not change over time. Of note, human embryonic stem cells showed the typical specific nuclear staining, but a few cells were found positive for Oct4 show cytoplasmic labeling, which appears to be the pattern of staining displayed by majority of menstrual blood-derived stem cells. While there is no solid explanation for such cytoplasmic labeling, this differential pattern of Oct4 labeling may distinguish ES cells from menstrual blood-derived stem cells. Furthermore, menstrual blood-derived stem cells (75%) were CXCR4 positive, a stem cell chemotaxis marker, also expressed by human embryonic stem cells.

ELISA

The timing of ELISA paralleled the hypoxic condition (i.e., OGD) using passage 6 or 9 and additionally cultured for 3 passages before testing, with the conditioned media collected at 2 days after OGD. Trophic factors such as vascular endothelial growth factor (VEGF), brain derived-neurotrophic factor (BDNF), and Neurotrophin-3 (NT-3), but not glial cell line-derived neurotrophic factor (GDNF) have been detected as critical secretory factors in stem cells. Thus, these molecules were measured as possible neurotrophic factors secreted by menstrual blood-derived stem cells. The media collected, as described above, served as samples for evaluation of trophic factor secretion. The levels of VEGF, BDNF, GDNF, and NT-3 released from 1 million adherent cells were determined using ELISA kits according to the protocols of the manufacturer (BDNF and GDNF from Promega; VEGF and NT-3 from R & D Systems). The conditioned media were analyzed by interpolation from the standard curves assayed on individual plates. The ELISA data showed elevated levels of trophic factors, such as VEGF, BDNF, and NT-3, in the media of OGD-exposed cultured menstrual blood-derived stem cells, seen in the Table.

TABLE

ELISA results of growth factor expression trophic factors, such as VEGF, BDNF, and NT-3, were upregulated in the media of OGD-exposed cultured menstrual blood-derived stem cells.

| Growth Factors | Concentration (pg/ml) |
|---|---|
| GDNF | Non-detectable (less than 3 pg/ml) |
| VEGF | 480.4 15.8 (n = 3) |
| BDNF | 97.47 (n = 2) |
| NT-3 | (n = 2) |

Cultured menstrual blood-derived cells express stem cell markers, and some exhibit neural markers. Menstrual blood-derived stem cells afford protection in co-cultured primary neurons subjected to experimental in vitro stroke. There were no significant differences in the protective effects afforded by co-culturing with menstrual blood-derived stem cells and exposure to the media collected from cultured menstrual blood-derived stem cells (p's>0.1). More importantly, transplantation of menstrual blood-derived stem cells, either directly into the brain or peripherally, ameliorated stroke-induced behavioral and histological deficits. These robust therapeutic effects of menstrual blood-derived stem cells make them appealing for cell therapy for stroke.

While OGD and normal culture conditions are two distinct culture conditions, because the present disease indication targeted stroke, the choice to demonstrate trophic factor secretion in the in vitro stroke OGD model is deemed a logical approach. Previous studies (Borlongan, et al. (2009). Hibernation-like state induced by an opioid peptide protects against experimental stroke. BMC Biol 7:31; Yasuhara, et al. (2009). Mannitol facilitates neurotrophic factor upregulation and behavioral recovery in neonatal hypoxic-ischemic rats with human umbilical cord blood grafts. J Cell Mol Med February 4), as well as those by several others (Slevin, et al. (2008). Leukaemia inhibitory factor is overexpressed by ischaemic brain tissue concomitant with reduced plasma expression following acute stroke. Eur J Neurol 15:29-37; Dimitrijevic, et al. (2006). Effects of the chemokine CCL2 on blood-brain barrier permeability during ischemia-reperfusion injury. J Cereb Blood Flow Metab 26:797-810; Katakowski, et al. (2007). Stroke-induced subventricular zone proliferation is promoted by tumor necrosis factor alpha-converting enzyme protease activity. J Cereb Blood Flow Metab 27:669-678; Chen, et al. (2005). Atorvastatin induction of VEGF and BDNF promotes brain plasticity after stroke in mice. J Cereb Blood Flow Metab 25:281-290; Xu, et al. (2000). Oxygen glucose deprivation induces inducible nitric oxide synthase and nitrotyrosine expression in cerebral endothelial cells. Stroke 31:1744-1751), have similarly employed experimental in vitro paradigms in providing insights into mechanistic pathway of neural repair in stroke. The present in vitro data provide evidence lending support to the notion that menstrual blood-derived stem cells likely exerted neuroprotection against stroke via a trophic factor mechanism. Consideration was given to clarify trophic factor secretion of transplanted stem cells in the in vivo setting (Yasuhara, et al. (2009). Mannitol facilitates neurotrophic factor upregulation and behavioral recovery in neonatal hypoxic-ischemic rats with human umbilical cord blood grafts. J Cell Mol Med February 4; Yasuhara, et al. (2009). Notch-induced rat and human bone marrow stromal cell grafts reduce ischemic cell loss and ameliorate behavioral deficits in chronic stroke animals. Stem Cells Dev [Epub ahead of print]; Borlongan, et al. (2004). Central nervous system entry of peripherally injected umbilical cord blood cells is not required for neuroprotection in stroke. Stroke 35:2385-2389), but the practical application of infusing conditioned medium, as opposed to transplanting stem cells, may be limited by product manufacturing, which likely poses as a challenge in obtaining therapeutic doses of cocktails of growth factors in ample supply to carry out large scale clinical trials. Moreover, the rationale to pursue the present experiments on neural differentiation in an in vitro setting resonates the guidelines set forth by STEPS (Stem cell Therapeutics as an Emerging Paradigm for Stroke; 5,6), in that the initial step for advancing cell therapy for stroke (or any disease indication for that matter) is by providing a phenotypic characterization of the donor cells.

EXAMPLE 2

In Vivo Analysis of Menstrual Blood-Derived Cell Treatment

Transient unilateral focal ischemia was produced using a well-established middle cerebral artery occlusion (MCAO) using the intraluminal suture model as previously described (Borlongan, et al. (1998) Transplantation of cryopreserved human embryonal carcinoma-derived neurons (NT2N cells) promotes functional recovery in ischemic rats. Exp Neurol 149:310-321; Borlongan, et al. (2000) Glial cell survival is enhanced during melatonin-induced neuroprotection against cerebral ischemia. FASEB J 14:1307-1317). Male Sprague-Dawley rats weighing about 250 g were anesthetized with gas inhalation composed of 30% oxygen (0.3 L/min) and 70% nitrous oxide (0.7 L/min) mixture. The gas was passed through an isoflurane vaporizer set to deliver 3% to 4% isoflurane during initial induction and 1.5% to 2% during surgery. Physiological parameters, via blood gases assays, and ischemia and reperfusion levels determined by laser Doppler measurements, did not differ among all MCAO stroke groups. The body temperature of animals was maintained at 37° C. during the surgery until they recovered from anesthesia. Based on pilot studies, a 60-minute MCAO produces a well-defined ischemic core and penumbra.

In order to further evaluate the therapeutic potential of menstrual blood-derived stem cells in stroke, the efficacy of transplanting these cells in an established in vivo rat stroke model was examined. Menstrual blood stem cells were grafted under aseptic conditions. For intracerebral (IC) transplantation in MCAO stroke animals, anesthetized animals (equithesin 3 ml/kg i.p.) were implanted with menstrual blood-derived stem cells directly into the striatum (0.5 mm anterior to bregma, 2.8 mm lateral to midline and 5.0 mm below the dural surface), using a 28-gauge implantation cannula (Borlongan, et al. (1998). Transplantation of cryopreserved human embryonal carcinoma-derived neurons (NT2N cells) promotes functional recovery in ischemic rats. Exp Neurol 149:310-321). For intravenous (IV) delivery, animals were anesthetized with 2% isoflurane in a jar for pre anesthetic, and spontaneously respired with 1.5% isoflurane in 2:1 N2O:O2 mixture using a facemask connected and regulated with a modified vaporizer. Accurate placement of a 27-gauge needle within the jugular vein was confirmed by aspirate of blood into the syringe. Cell volume was preset at 400 k in 3 µl solution (PBS) and 4 million cells in 1 ml solution (PBS) for IC and IV transplantation, respectively. The rationale for the current IC and IV doses is based on work with similar stem/progenitor cell therapeutic doses, including bone marrow, umbilical cord blood, and fetal tissue-derived cells (Yasuhara, et al. (2009). Notch-induced rat and human bone marrow stromal cell grafts reduce ischemic cell loss and ameliorate behavioral deficits in chronic stroke animals. Stem Cells Dev [Epub ahead of print]; Borlongan, et al. (2004). Central nervous system entry of peripherally injected umbilical cord blood cells is not required for neuroprotection in stroke. Stroke 35:2385-2389; Hara, et al. (2007). Transplantation of post-mitotic human neuroteratocarcinoma overexpressing Nurr1 cells provides therapeutic benefits in experimental stroke: in vitro evidence of expedited neuronal differentiation and GDNF secretion. J Neurosci Res 85:1240-1251; Yasuhara, et al. (2006). Transplantation of human neural stem cells exerts neuroprotection in a rat model of Parkinson's disease. J Neurosci 26:12497-12511). Delivery was via manual infusion with an infusion rate approximately at 1 µl or 1 ml per minute, respectively. Cryopreserved cells were obtained from Cryo-Cell International Inc. and thawed just prior to transplantation surgery.

Viability cell counts, using Trypan Blue exclusion method, were conducted prior to transplantation and immediately after the transplantation on the last animal recipient. The cell viability criterion of at least 80% viable cells was used to proceed with the transplantation surgery. The pre-determined cell dosages refer to number of viable cells. Transplantation surgery was carried out within 2 hours post-stroke, and timed with thawing of the cells. A heating pad and a rectal thermometer allowed maintenance of body temperature at about 37° C. throughout surgery and following recovery from anesthesia. In each treatment group, 4-5 animals were randomly assigned to receive either cells from passage 6 or 9, with both cells further cultured for 3 passages before testing. The original sample size was 10 rats per group, but 3 animals died during and/or immediately after stroke surgery, thus the study included the following subjects in each treatment condition: IV (n=9), IC (n=10), and Vehicle (n=8). Four animals received IC vehicle and another 4 animals received IV vehicle. Behavioral and histological analyses between these two control groups revealed tight behavioral scores and cell counts, without any significant statistical differences, thus data from both groups were combined and treated as one group.

Behavioral assessment estimation was performed by using semi quantitative analysis of motor asymmetry (elevated body swing test, EBST), (Borlongan, et al. (1998). Transplantation of cryopreserved human embryonal carcinoma-derived neurons (NT2N cells) promotes functional recovery in ischemic rats. Exp Neurol 149:310-321; Borlongan, et al. (2000). Glial cell survival is enhanced during melatonin-induced neuroprotection against cerebral ischemia. FASEB J 14:1307-1317; Borlongan, et al. (2009). Hibernation-like state induced by an opioid peptide protects against experimental stroke. BMC Biol 7:31), motor coordination (Cylinder test) (Yasuhara T, Matsukawa N, Hara K, Yu G, Xu L, Maki M, Kim S U, Borlongan C V. (2006). Transplantation of human neural stem cells exerts neuroprotection in a rat model of Parkinson's disease. J Neurosci 26:12497-12511), and neurological function (Bederson test) at 14 days after stroke-transplantation surgery. To prevent any examiner's bias, all behavioral evaluations were performed by an investigator blinded to the treatment conditions.

The EBST provided a motor asymmetry parameter. The test apparatus consisted of a clear Plexiglas box (40×40×35.5 cm). The animal was gently picked up at the base of the tail, and elevated by the tail until the animal's nose is at a height of 2 inches (5 cm) above the surface. The direction of the swing, either left or right, was counted once the animals head moved sideways approximately 10 degrees from the midline position of the body. After a single swing, the animal was placed back in the Plexiglas box and allowed to move freely for 30 seconds prior to retesting. These steps were repeated 20 times for each animal, with performance expressed in percentage to show the biased swing activity.

The cylinder test was used to assess the degree of forepaw asymmetry. Rats were placed in a transparent cylinder (diameter: 20 cm, height: 30 cm) for 3 minutes with the number of forepaw contacts to the cylinder wall counted. The score of cylinder test in this study was calculated as a contralateral bias, that is, [(the number of contacts with the contralateral limb)−(the number of contacts with the ipsilateral limb)/(the number of total contacts)×100].

The Bederson test is conducted by assigning a neurologic score for each rat obtained from a battery of 4 tests which included (1) observation of spontaneous ipsilateral circling, graded from 0 (no circling) to 3 (continuous circling); (2) contralateral hindlimb retraction, which measured the ability of the animal to replace the hindlimb after it was displaced laterally by 2 to 3 cm, graded from 0 (immediate replacement) to 3 (replacement after minutes or no replacement); (3) beam walking ability, graded 0 for a rat that readily traversed a 2.4-cm-wide, 80-cm-long beam to 3 for a rat unable to stay on the beam for 10 seconds; and (4) bilateral forepaw grasp, which measured the ability to hold onto a 2-mm-diameter steel rod, graded 0 for a rat with normal forepaw grasping behavior to 3 for a rat unable to grasp with the forepaws.

Figure 6:
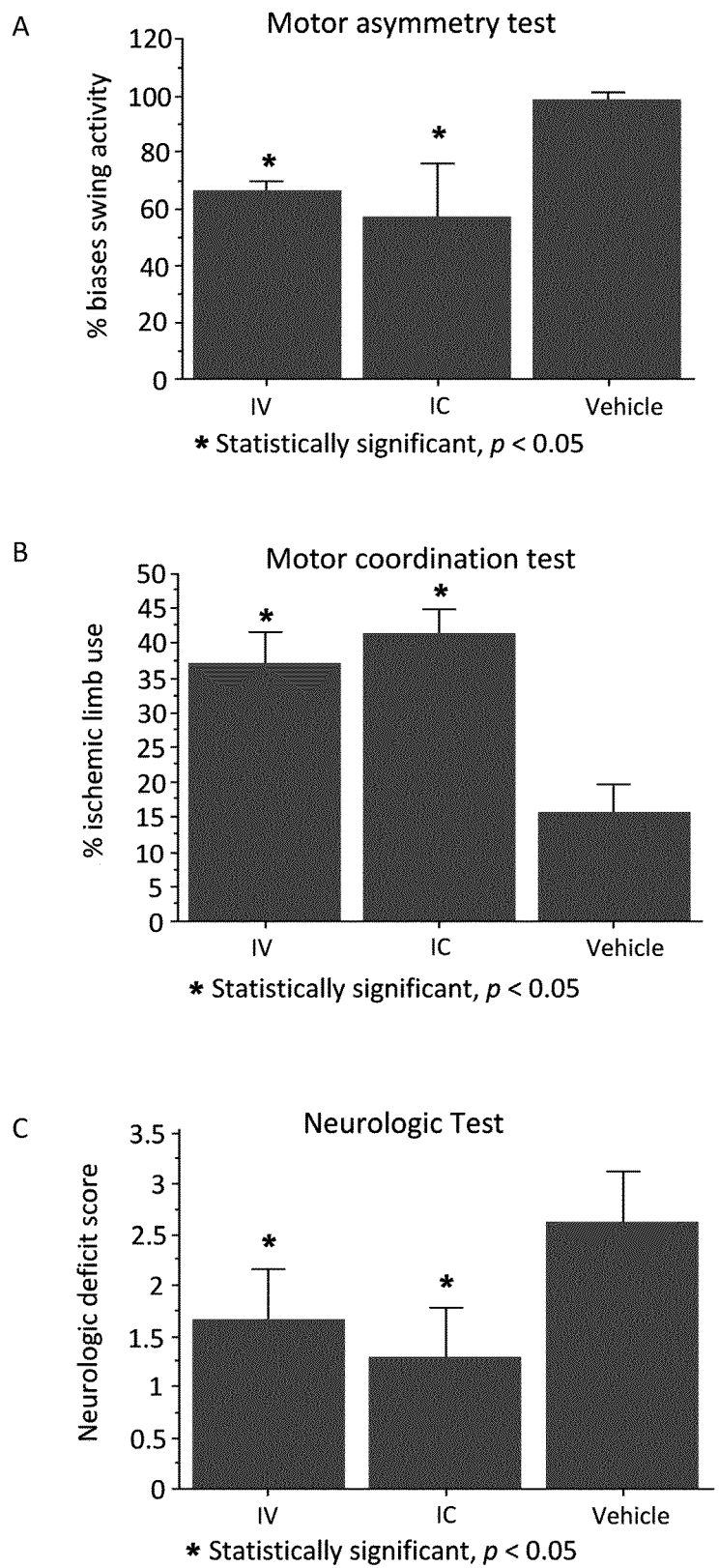
FIGS. 6(a)-(c) are graphs showing transplanted menstrual blood-derived stem cells rescue against in vivo stroke injury. Transplantation of menstrual blood-derived stem cells, either intracerebrally (IC) or intravenously (IV), after experimentally induced ischemic stroke in adult rats significantly reduced behavioral abnormalities for (A) motor asymmetry, (B) motor coordination and (C) neurological performance, compared to vehicle-infused rats. Error bars represent standard deviations. Asterisk * corresponds to statistically significant difference between IC or IV delivered menstrual blood-derived stem cells and control; however, in the motor coordination test, IC shows significantly better recovery of ischemic limb compared to IV.
Figure 7:
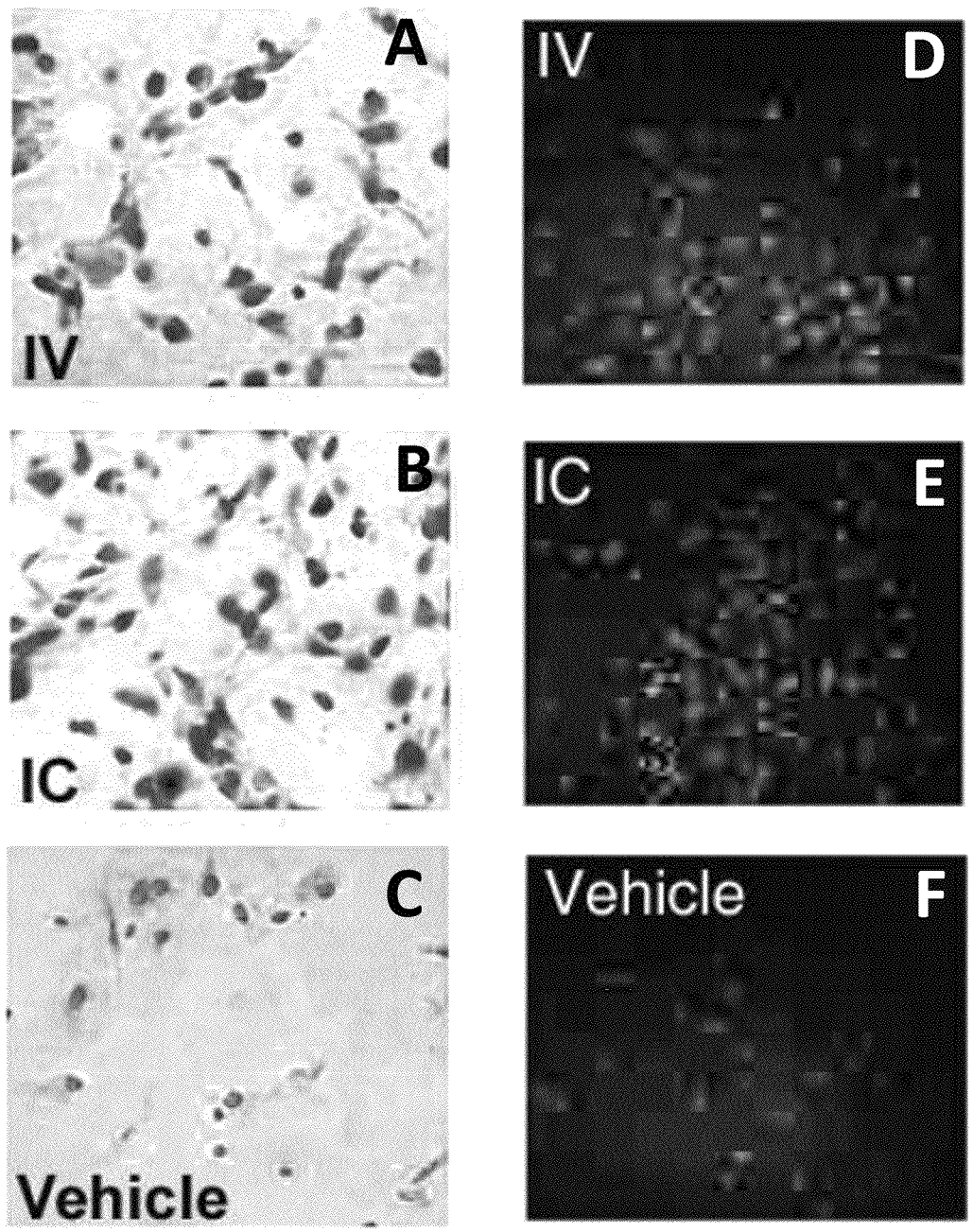
FIGS. 7(a)-(f) are images showing transplanted menstrual blood-derived stem cells increase survival of host cells within the ischemic penumbra. Histological and immunohistochemical examination using H&E (A) through (C) and DAPI staining (D) through (F) revealed that there were more surviving host cells in the striatal ischemic penumbra of stroke animals that received either IC and IV transplantation of menstrual blood-derived stem cells compared to those that received IC (shown) or IV vehicle infusion (* p's<0.0001).

The scores from all 4 tests, which were done over a period of about 15 minutes, were added to give a neurologic deficit score (maximum possible score of 12 points from the 4 component tests). In order to determine significant differences in behavioral deficits and ischemic cell loss, data were analyzed using ANOVA followed by post hoc Fisher's test. Statistical significance was preset at $p<0.05$. ANOVA revealed significant treatment effects in all 3 behavioral tests (EBST, F2,24=29.71, p<0.0001; Cylinder test, F2,24=103-87, p<0.0001; and Bederson test, F2,24=16.27, p<0.0001), with posthoc t-tests showing that both IC- and IV-delivered menstrual blood-derived stem cells ameliorated these motor and neurological impairments. In addition, both IC and IV route produced the same degree of behavioral recovery in EBST and Bederson Test (p's>0.1), but direct transplantation into the stroke brain promoted significantly better improvement of motor coordination in the Cylinder Test than peripheral administration (p<0.05). Transplantation of menstrual blood-derived stem cells, either intracerebrally (IC) or intravenously (IV), after experimentally induced ischemic stroke in adult rats significantly reduced behavioral abnormalities compared to vehicle-infused rats, as seen in FIGS. 6(a)-(c).

Figure 8:
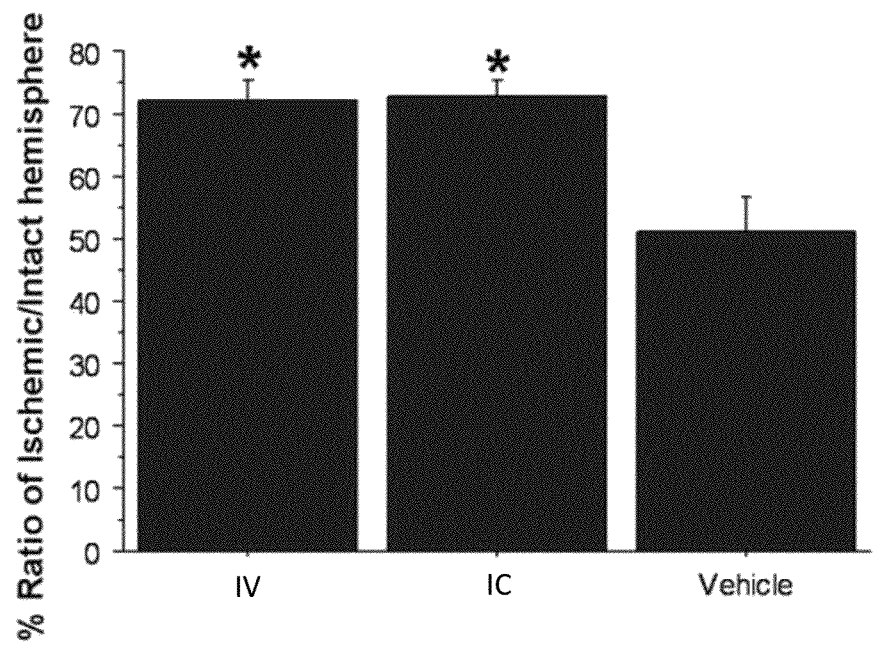
FIG. 8 is a graph showing transplanted menstrual blood-derived stem cells increase survival of host cells within the ischemic penumbra. Analysis revealed that there were more surviving host cells in the striatal ischemic penumbra of stroke animals that received either IC and IV transplantation of menstrual blood-derived stem cells compared to those that received IC (shown) or IV vehicle infusion (* p's<0.0001). Error bars represent standard deviations. Asterisk * corresponds to statistically significant difference between IC or IV delivered menstrual blood-derived stem cells and control.
Figure 9:
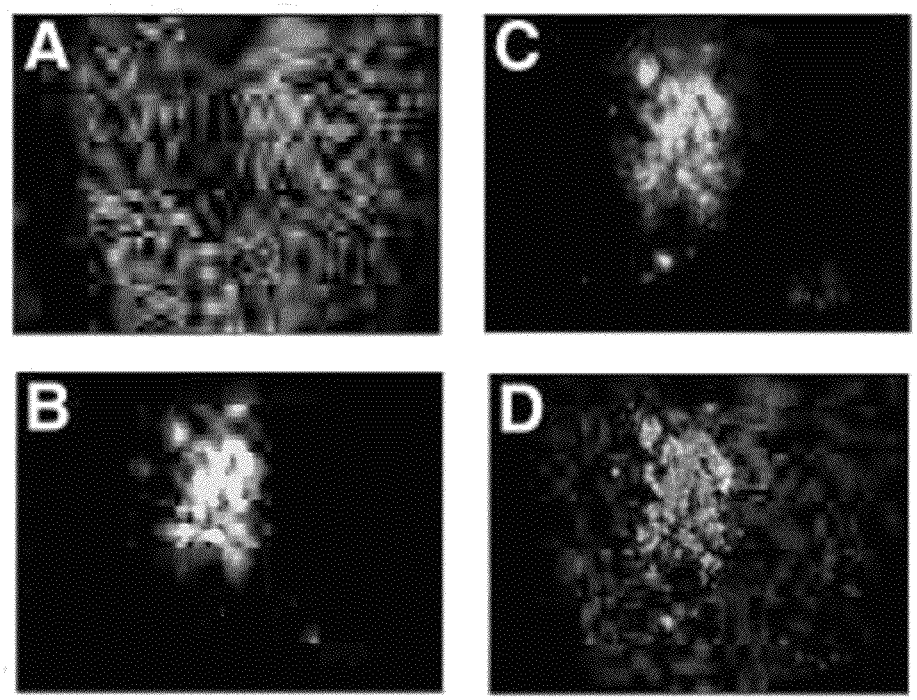
FIGS. 9(a)-(d) are images showing transplanted menstrual blood-derived stem cells survive in the stroke brain. Immunofluorescent microscopy evaluation of the status of grafted cells revealed that menstrual blood-derived stem cells transplanted intracerebrally survived in the stroke rat brain (ischemic penumbra). At 14 days after transplantation, IC delivered menstrual blood-derived stem cells (HuNu positive) were detected in the ischemic striatal penumbra within the original transplant site. Staining was performed with (A) DAPI; (B) HuNu; (C) Oct4; and (D) merged. Most of the cells (>80%) retained their stem cell marker (Oct4). Approximate graft survival rates were 15% for IC delivered cells. Scale bar=10 μm.
Figure 10:
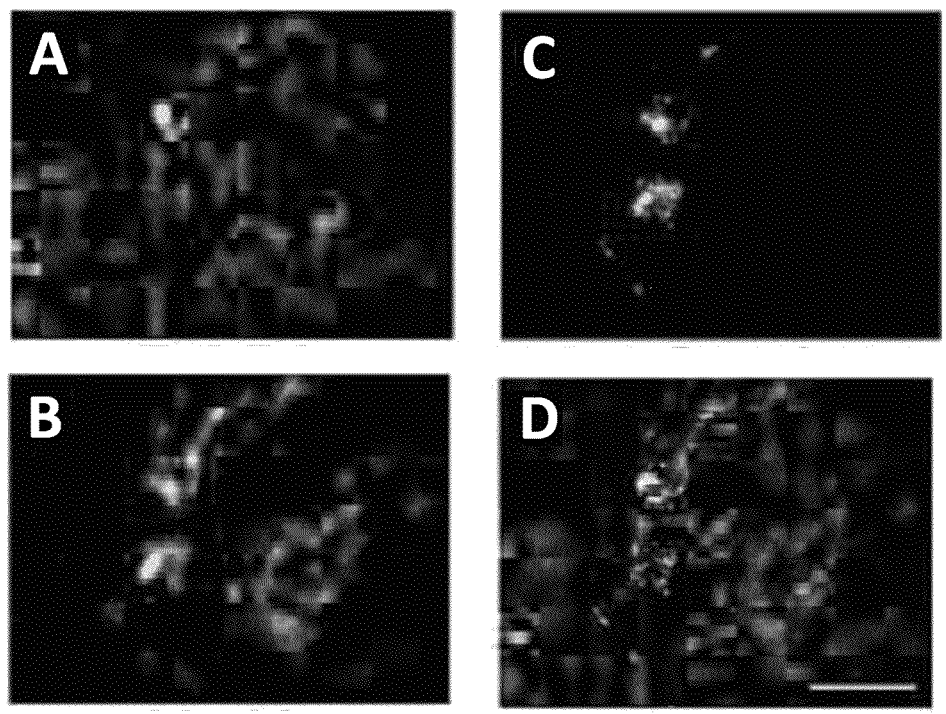
FIGS. 10(a)-(d) are images showing transplanted menstrual blood-derived stem cells survive in the stroke brain. Immunofluorescent microscopy evaluation of the status of grafted cells revealed that menstrual blood-derived stem cells transplanted intracerebrally survived in the stroke rat brain (ischemic penumbra). At 14 days after transplantation, IC delivered menstrual blood-derived stem cells (HuNu positive) were detected in the ischemic striatal penumbra a short distance away from the original transplant site. Staining was performed with (A) DAPI; (B) HuNu; (C) Oct4; and (D) merged. Most of the cells (>80%) retained their stem cell marker (Oct4). Approximate graft survival rates were 15% for IC delivered cells. Scale bar=10 μm.
Figure 11:
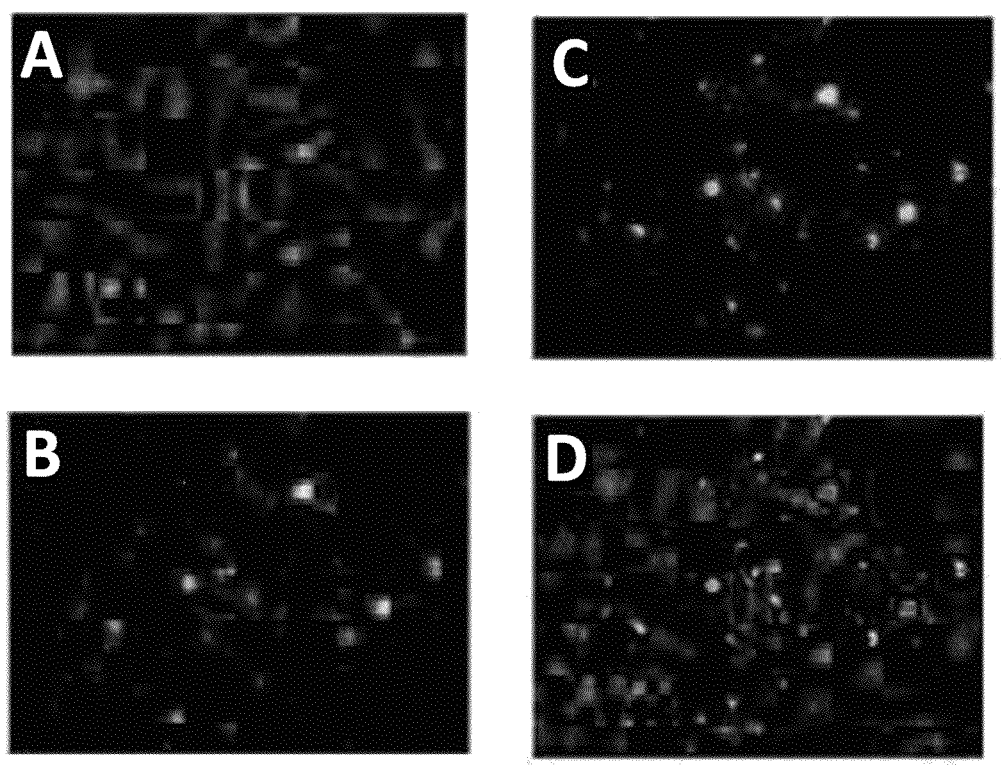
FIGS. 11(a)-(d) are images showing transplanted menstrual blood-derived stem cells survive in the stroke brain. Immunofluorescent microscopy evaluation of the status of grafted cells revealed that menstrual blood-derived stem cells transplanted intravenously survived in the stroke rat brain (ischemic penumbra). At 14 days after transplantation, IV delivered menstrual blood-derived stem cells (HuNu positive) were detected in the ischemic striatal penumbra within the original transplant site. Staining was performed with (A) DAPI; (B) HuNu; (C) Oct4; and (D) merged. Most of the cells (>90%) retaining their stem cell marker (Oct4). Approximate graft survival rates were less than 1% for IV delivered cells. Scale bar=10 μm.
Figure 12:
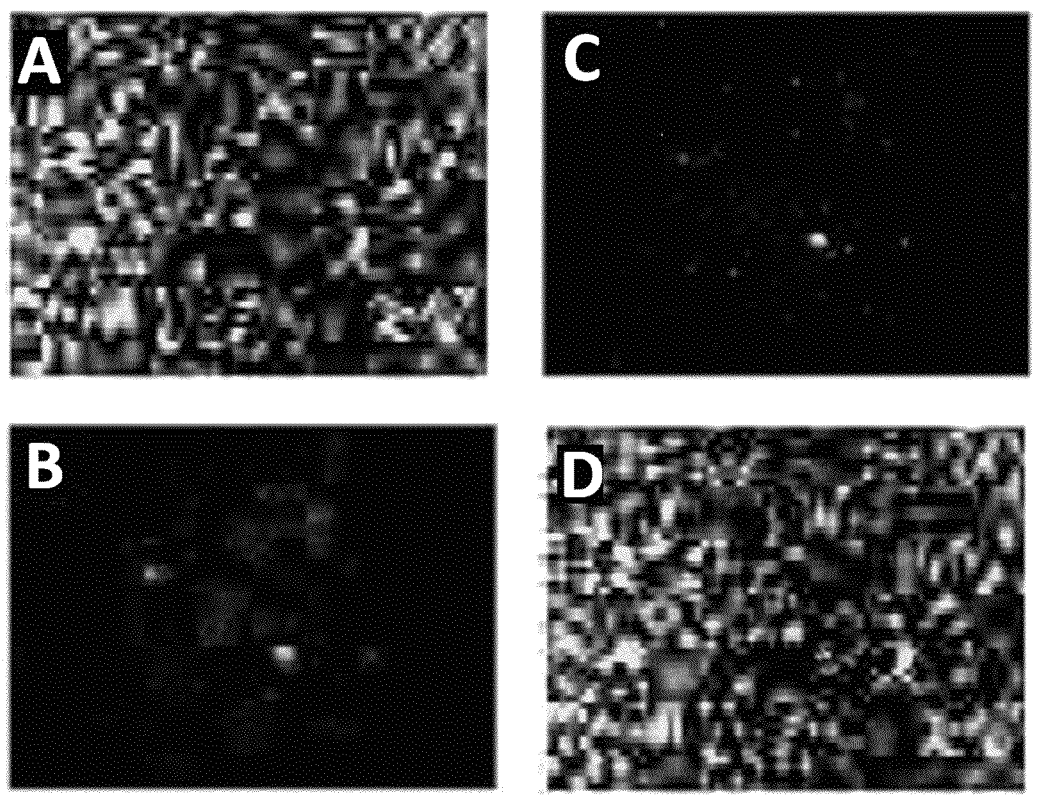
FIGS. 12(a)-(d) are images showing transplanted menstrual blood-derived stem cells survive in the stroke brain. Immunofluorescent microscopy evaluation of the status of grafted cells revealed that menstrual blood-derived stem cells transplanted intravenously survived in the stroke rat brain (ischemic penumbra). At 14 days after transplantation, IV delivered menstrual blood-derived stem cells (HuNu positive) were detected in the inner boundary of the ischemic striatal penumbra. Staining was performed with (A) DAPI; (B) HuNu; (C) Oct4; and (D) merged. Most of the cells (>90%) retaining their stem cell marker (Oct4). Approximate graft survival rates were less than 1% for IV delivered cells. Scale bar=10 μm.

Under deep anesthesia, rats were sacrificed at 14 days after reperfusion, and perfused through the ascending aorta with 200 ml of cold PBS, followed by 100 ml of 4% PFA in PBS. Brains were removed and post-fixed in the same fixative for 3 days followed by 30% sucrose in phosphate buffer (PB) for 1 week. Six series of coronal sections were cut at a thickness of 30 µm by cryostat and stored at −20° C. Free floating sections for immunohistochemistry were incubated overnight at 4° C. with anti-MAP2 polyclonal antibody (1:500, Chemicon), anti-HuNu, and anti-Oct4 with 10% normal goat serum. After several rinses in PBS, the sections were visualized following the method described above with modification to accelerate FITC with biotin conjugated anti-mouse IgG antibody and FITC conjugated streptoavidin (1:500, Sigma, MO). Control studies included exclusion of primary antibody substituted with 10% normal goat serum in PBS. No immunoreactivity was observed in these controls. Finally, brain sections were counterstained with DAPI. Immunofluorescent and light microscopy were carried out using Zeiss Axiophot 2, as seen in FIGS. 7(a)-(f). Sections were blind-coded and Abercrombie's formula was used to calculate the total number of immunopositive cells. (Abercrombie Correction=C*(T/T+N), where C is crude cell counts, T is the section thickness and N is mean nucleus size) (Abercrombie & Johnson (1946). Quantitative histology of Wallerian degeneration I. Nuclear population in rabbit sciatic nerve. J Anat 80:37-50). Immunohistochemical examination of the DAPI immunostaining revealed that there were more surviving host cells in the striatal ischemic penumbra of stroke animals that received either IC and IV transplantation of menstrual blood-derived stem cells compared to those that received vehicle infusion (ANOVA F2,24=55.91, p<0.0001; posthoc t-tests: IV or IC vs. controls, p's<0.0001; no significant difference between IC and IV, p>0.05), as seen in FIG. 8.

Immunofluorescent microscopy evaluation of the status of grafted cells revealed that menstrual blood-derived stem cells either transplanted intracerebrally or intravenously survived in the stroke rat brain (ischemic penumbra). At 14 days after transplantation, IC delivered menstrual blood-derived stem cells (HuNu positive) were detected in the ischemic striatal penumbra within and a short distance away from the original transplant site, seen in FIGS. 9(a) through 13(b). Most of the cells (>80%) retained their stem cell marker (Oct4). Similarly, IV delivered menstrual blood-derived stem cells (HuNu positive) were detected in the inner and outer boundary of the ischemic striatal penumbra, with most of the cells (>90%) retaining their stem cell marker (Oct4). Approximate graft survival rates were 15% and less than 1% for IC and IV delivered cells, respectively.

The density of endogenous cells in the ischemic penumbra (determined by DAPI stain using consecutive sections) was estimated and analyzed as described previously (Matsukawa, et al. (1999) Increased expression of hippocampal cholinergic neurostimulating peptide-related components and their messenger RNAs in the hippocampus of aged senescence-accelerated mice. Neuroscience 88: 79-92; Yasuhara, et al. (2005) Early transplantation of an encapsulated glial cell line-derived neurotrophic factor-producing cell demonstrating strong neuroprotective effects in a rat model of Parkinson disease. J Neurosurg. 102:80-89). Briefly, the level of +0.2 mm anterior to the bregma based on the atlas of Paxinos and Watson (Paxinos and Watson, (1998) The Rat Brain in Stereotaxic Coordinates. San Diego: Academic Press) was selected for semi-quantitative analysis. Based on pilot studies, this brain area consistently exhibits the ischemic striatal penumbra following a 60-minute MCAO. For estimation of DAPI-positive cells, two striatal areas (each area: 0.05 mm2) in the ischemic penumbra and symmetrical two areas in the contralateral side were analyzed using Scion Image software (Scion Corp., MD). The areas were captured, binary images created with a distinct threshold, and positive areas calculated and summed up. The ratio of lesion to intact side was used for statistical analyses. For estimation of graft survival, the number of HuNu-positive cells were counted in six consecutive 0.05 mm2 regions of the inner and outer boundary zone of striatal penumbra. The total number of HuNu-positive cells in the six areas was counted and expressed as cells/mm2 for statistical analyses. Similarly, for determining whether the HuNu positive cells remained as stem cells or differentiated into a neuronal lineage, double-labeling with Oct4 and MAP2 was examined in the same striatal ischemic penumbra as described above.

The existence of a population of stem cells in the intact endometrium that were believed to die and later shed during the menstrual cycle has been suggested 30 years ago (Prianishnikov (1978). On the concept of stem cell and a model of functional morphological structure of the endometrium. Contraception 18:213-223). However, not until recently did a study show that adherent cells derived from the endometrium are capable of differentiating into 9 lineages, namely, cardiomyocytic, respiratory epithelial, neurocytic, myocytic, endothelial, pancreatic, hepatic, adipocytic, and osteogenic cells (Meng, et al. (2007). Endometrial regenerative cells: a novel stem cell population. J Transl Med 15; 5:57). In parallel, stromal cells harvested from menstrual blood display multipotent markers such as Oct-4, SSEA-4, and c-kit at the molecular and cellular level (Patel, et al. (2008). Multipotent Menstrual Blood Stromal Stem Cells: Isolation, characterization and differentiation. Cell Transplant 17:303-311). In addition, menstrual blood-derived mesenchymal cells have been demonstrated to differentiate into cardiac precursor-like cells (Hida, et al. (2008). Novel cardiac precursor-like cells from human menstrual blood-derived mesenchymal cells. Stem Cells 26:1695-1704). These adherent, stromal, and mesenchymal cells appear to exhibit characteristics similar to stem cells derived from the endometrium present in the menstrual blood, which have been implicated to contribute to endometrial regeneration (Du & Taylor (2007). Contribution of Bone Marrow-Derived Stem Cells to Endometrium and Endometriosis. Stem Cells 25: 2082-2086). Not all the endometrium is shed; the basal layer remains, where endometrial stem/progenitor cells are thought to reside. However, equally compelling evidence from a recent study identifies partially purified endometrial mesenchymal stem cell-like cells incorporated within the functional layer that is shed (Schwab & Gargett (2007). Co-expression of two perivascular cell markers isolates mesenchymal stem-like cells from human endometrium. Hum Reprod 22:2903-2911). This would perhaps explain why some endometrial mesenchymal stem cell-like cells are present in menstrual blood in addition to the stromal fibroblasts present in human endometrium. Based on the stem cell markers employed here (Oct4, Nanog, SSEA and CXCR4), both menstrual blood-derived stem cells and bone marrow stem cells appear to share similar phenotypic properties.

Despite robust differentiation of menstrual blood-derived stem cells into cardiac cells (Hida, et al. (2008). Novel cardiac precursor-like cells from human menstrual blood-derived mesenchymal cells. Stem Cells 26:1695-1704), they seem to have limited ability to commit into neuronal lineage as shown in the present study. Although pathophysiological symptoms of stroke and cardiac arrest significantly overlap (e.g., tissue infarcts), a major difference between the two diseases is the underlying cell damage, i.e., muscles versus neurons. This host environmental niche has been shown to participate in directing the lineage commitment of transplanted stem cells, thereby differentially regulating the eventual fate of menstrual blood-derived stem cells. The enhanced tendency of menstrualblood-derived stem cells to commit more preferentially to cardiomyocytes when transplanted to the ischemic heart over neuronal differentiation following transplantation into the stroke brain may be due to the relative tissue-specific differentiation signals rendered by the injured organ, which can be highly time-dependent post-injury. The original source of the stem cells may also likely dictate their lineage commitment. In particular, menstrual blood stem cells may be derived from the endometrial mucosa lined with a luminal epithelium from which glands extend to the myometrial layer through a supportive stromal tissue. The glands are lined by a pseudostratified columnar epithelium. Accordingly, the biased potency of menstrual blood stem cells to commit towards muscle cells, i.e., cardiomyocytes over neural cells may have been a pre-destined process even prior to transplantation. In the end, host microenvironmental cues and tissue origins of the stem cells, among other factors (diseased state), may contribute to the differentiation of transplanted stem cells.

The exact mechanism underlying the observed functional benefits of menstrual blood-derived stem cells remains to be determined. However, the retention of stem-like phenotypic characteristics by menstrual blood-derived stem cell grafts coinciding with immediate behavioral recovery at an early period after transplantation, suggests that a bystander effect rather than a cell replacement via neuronal differentiation mechanism likely mediates the observed therapeutic benefits of this cell transplant regimen. Indeed, examination of trophic factor levels in the media of OGD-exposed cultured menstrual blood-derived stem cells reveals that upregulation of VEGF, BDNF, NT-3, but not GDNF. Conversely, umbilical cord blood cell studies indicate that neutralization of GDNF, BDNF and neural growth factor (NGF) eliminated the umbilical cord blood cell's stroke treatment abilities, as seen in Borlongan, et al. (U.S. application Ser. No. 11/012,849). Recent reports have implicated this set of trophic factors as mediating therapeutic benefits of transplanted stem cells in a variety of CNS disorders, including stroke (Lee, et al. (2007). Human neural stem cells over-expressing VEGF provide neuroprotection, angiogenesis and functional recovery in mouse stroke model. PLoS ONE 17; 2:e156; Hau, et al. (2008). Evidence for neuroprotective properties of human umbilical cord blood cells after neuronal hypoxia in vitro. BMC Neurosci 29; 9:30; Nomura, et al. (2005). I.V. infusion of brain-derived neurotrophic factor gene-modified human mesenchymal stem cells protects against injury in a cerebral ischemia model in adult rat. Neuroscience 136:161-169; Kurozumi, et al. (2005). Mesenchymal stem cells that produce neurotrophic factors reduce ischemic damage in the rat middle cerebral artery occlusion model. Mol Ther 11:96-104; Pisati, et al. (2007). Induction of neurotrophin expression via human adult mesenchymal stem cells: implication for cell therapy in neurodegenerative diseases. Cell Transplant 16:41-55; Wang, et al. (2008). Neural progenitor cells treated with EPO induce angiogenesis through the production of VEGF. J Cereb Blood Flow Metab 28:1361-1368). However, most of these compounds have been examined as a monotherapy, and clinical trials, at least for GDNF treatment in Parkinson's disease, have been mixed (Slevin, et al. (2007). Unilateral intraputamenal glial cell line-derived neurotrophic factor in patients with Parkinson disease: response to 1 year of treatment and 1 year of withdrawal. J Neurosurg 106:614-620; Matcham, et al. (2007). GDNF in Parkinson's disease: the perils of post-hoc power. J Neurosci Methods 163:193-196; Hutchinson, et al. (2007). GDNF in Parkinson disease: an object lesson in the tyranny of type II. J Neurosci Methods 163:190-192). The ability of menstrual blood-derived cells to secrete a cocktail of growth factors and the cells' potential to respond to host cues as well as to stimulate the microenvironment are deemed more advantageous than the exogenous application of these growth factors.

The observation that IV transplanted animals displayed functional recovery equal to IC transplanted animals despite less donor cell graft survival bolsters the hypothesis that graft survival per se is not the primary mode of action of the cells. Indeed, it has previously been shown that the entry of grafted cells (i.e., umbilical cord blood derived cells) is not a prerequisite for behavioral recovery of transplanted stroke animals. Neurotrophic factor secretion by the graft, the host, or combination of both is likely the key neuroprotective mechanism underlying the therapeutic benefits of menstrual blood-derived stem cells. Moreover, it is logical to think that IV administered menstrual blood-derived stem cells possess similar safety and toxicity profile as IV delivered CXCR4 positive stem cells derived from bone marrow and umbilical cord. To date, no deleterious side effects have been reported with any of these CXCR4 positive cells. Moreover, following stroke, the ligand of CXCR4, SDF-1, is elevated in the brain, allowing a chemotactic signaling pathway for these cells to hone preferentially towards the ischemic brain site from the periphery (Shyu, et al. (2008). Stromal cell-derived factor-1 alpha promotes neuroprotection, angiogenesis, and mobilization/ homing of bone marrow-derived cells in stroke rats. J Pharmacol Exp Ther 324:834-849; Ohab, et al. (2006). A neurovascular niche for neurogenesis after stroke. J Neurosci 26:13007-13016). The deposition of these cells in peripheral organs may also be beneficial; for example, the anti-inflammatory function of the spleen implicated as an exacerbating factor in stroke progression can be blocked by grafted cells lodging into this organ resulting in reduction of stroke-induced inflammation and neurobehavioral deficits (Vendrame, et al. (2006). Cord blood rescues stroke-induced changes in splenocyte phenotype and function. Exp Neurol 199:191-200; Schwarting, et al. (2008). Hematopoietic stem cells reduce post-ischemic inflammation and ameliorate ischemic brain injury. Stroke 39:2867-2875).

Equally an important finding in this study is the safety of transplanting human menstrual blood-derived stem cells in an animal stroke model. There is no instance of detectable tumor or ectopic formation, as well as overt graft-versus-host complications in any of the transplanted animals, despite the absence of immunosuppression in this xenograft (i.e., cross species) transplantation paradigm. Subsequent studies should also be designed to reveal the immune status of the host especially in view of the lack of immunosuppression in this xenogeneic transplant paradigm. Gross examination of the transplanted site demonstrated no overt inflammatory response (via Nissl and H & E stains), which might have been mediated by the CNS harboring a partially immunoprivileged property, but more importantly the potential for menstrual blood-derived stem cells to exert immunosuppressive effects, as seen with bone marrow- and umbilical cord blood-derived stem cells (Yasuhara, et al. (2009). Mannitol facilitates neurotrophic factor upregulation and behavioral recovery in neonatal hypoxic-ischemic rats with human umbilical cord blood grafts. J Cell Mol Med February 4; Yasuhara, et al. (2009). Notch-induced rat and human bone marrow stromal cell grafts reduce ischemic cell loss and ameliorate behavioral deficits in chronic stroke animals. Stem Cells Dev [Epub ahead of print]; Borlongan, et al. (2004). Central nervous system entry of peripherally injected umbilical cord blood cells is not required for neuroprotection in stroke. Stroke 35:2385-2389). Interestingly, menstrual blood-derived stem cells also contain the same markers that have been identified on mesenchymal stem cells known for their immunosuppressive effect such as CD29, CD44, CD73, CD90, and CD105. Pilot studies also showed that these menstrual blood-derived stem cells in a mixed lymphocyte reaction demonstrated a very weak stimulatory response. Given the fact that the uterus lining does not reject allogeneic fetuses, it is likely that menstrual blood-derived stem cells may afford such immunosuppressive effects. Finally, graft-versus-host complications normally accompany xenografts (Borlongan, et al. (1998). Transplantation of cryopreserved human embryonal carcinoma-derived neurons (NT2N cells) promotes functional recovery in ischemic rats. Exp Neurol 149:310-321; Hara, et al. (2007). Transplantation of post-mitotic human neuroteratocarcinoma overexpressing Nurr1 cells provides therapeutic benefits in experimental stroke: in vitro evidence of expedited neuronal differentiation and GDNF secretion. J Neurosci Res 85:1240-1251; Hara, et al. (2008). Neural progenitor NT2N cell lines from teratocarcinoma for transplantation therapy in stroke. Prog Neurobiol 85:318-334), thus the absence of any overt graft rejection in the present cross-species paradigm parallels similar observations seen with human bone marrow-, amnion-, and umbilical cord blood-derived stem/progenitor cells (Yasuhara, et al. (2009). Notch-induced rat and human bone marrow stromal cell grafts reduce ischemic cell loss and ameliorate behavioral deficits in chronic stroke animals. Stem Cells Dev [Epub ahead of print]; Borlongan, et al. (2004). Central nervous system entry of peripherally injected umbilical cord blood cells is not required for neuroprotection in stroke. Stroke 35:2385-2389; Yasuhara, et al. (2006). Transplantation of human neural stem cells exerts neuroprotection in a rat model of Parkinson's disease. J Neurosci 26:12497-12511; Yu, et al. (2009). Amnion: a potent graft source for cell therapy in stroke. Cell Transplant 18:111-118); the latter cells' ability to circumvent host immune response has been suggested to be due to the immature immune system of these grafted cells or their capacity to secrete immunosuppressant factors.

The lack of tumor formation in the transplanted menstrual blood-derived stem cells is interesting in view of the observed Oct4+ labeling of majority of these cells. Whereas Oct4 has been used as a marker of pluripotent embryonic stem cells, the ability of these cells to form tumors may be affected by the immune status of the transplant recipient. The routine functional assay for determining pluripotency of Oct4-positive stem cells is to demonstrate teratoma formation in immunodeficient mice. Here, transplant recipients comprised of non-immunosuppressed rats. Moreover, the present subacute post-transplant period (14 days) and the diseased (stroke) state of the host brain might have contributed to the Oct4-labeled menstrual blood-derived stem cells to not fully manifest their pluripotent features. Alternatively, these cells might be expressing the Oct4 marker, but not truly exhibiting pluripotent features, including teratoma formation, thereby distinguishing them from the embryonic stem cells with robust tumorgenic potential. Indeed, other non-embryonic stem cells such as amnion-derived cells, express Oct4 but appear not to form tumors in vivo (De Coppie, et al. (2007). Isolation of amniotic stem cell lines with potential for therapy. Nat Biotechnol 25:100-106). This topic of Oct4 labeling of menstrual blood stem cell grafts requires a series of studies to unravel their relatively dormant proliferative status.

Compared to other sources of adult stem cells, such as bone marrow and umbilical cord blood, the menstrual blood offers relative ease of use and a wider window of harvesting the cells (i.e., cord blood only available during birth). Such ready availability and cryopreservable features of menstrual blood-derived stem cells should allow the entry of autologous transplantation for large scale clinical application.

The present data suggest that stem/progenitor cells shed during menstruation can be retrieved from menstrual blood and that they may provide a novel autologous source of adult stem cell for neural regeneration in women. Finding the male counterpart of these stem/progenitor cells (e.g., testis-derived cells) will further advance the potential for autologous transplantation. Of interest, testis-derived Sertoli cells stand as efficacious transplantable cells for CNS disorders (Sanberg, et al. (1996). Testis-derived Sertoli cells survive and provide localized immunoprotection for xenografts in rat brain. Nat Biotechnol 14:1692-1695; Sanberg, et al. (1997). Testis-derived Sertoli cells have a trophic effect on dopamine neurons and alleviate hemiparkinsonism in rats. Nat Med 3:1129-1132), although Sertoli cells are likely not stem cells. Sex-specific stem cell sources may reveal an evolutionary gender difference. Notwithstanding, the use of menstrual blood-derived stem cells for allogeneic transplantation may be an equally potential approach to cell therapy, along the line of investigations on therapeutic indications rendered by stem cells harvested from umbilical cord or bone marrow. Of note, menstrual blood-derived stem cells, referred to as Endometrial Regenerative Cells (ERC), have been shown to be safe when transplanted intravenously and intrathecally in 4 patients with multiple sclerosis, characterized by absence of immunological reactions or treatment associated adverse effects (Zhong, et al. (2009). Feasibility investigation of allogeneic endometrial regenerative cells. J Transl Med 7:15).

A small number of cell passages is the logistically preferred approach for clinical application. The present menstrual blood-derived stem cells were transferred to the study at passage 6 or 9 and cultured in the laboratory prior to infusion for an additional 3 passages so the cells were confirmed to be at passage 9 or 12 at the time of transplantation. Additional studies are warranted to determine cell phenotypes over multiple passages, although menstrual blood-derived stem cells continued to maintain expression of embryonic stem cell-like phenotypes up to at least 20 passages (unpublished data).

Menstrual blood-derived stem cells recapitulate the pluripotency properties, but circumvent the ethical and logistical limitations of embryonic stem cells. In vitro and in vivo assessment of transplanting menstrual blood-derived stem cells reveals their efficacy and safety in stroke, and stand as an alternative graft source for cell therapy in other CNS disorders.

In the preceding specification, all documents, acts, or information disclosed do not constitute an admission that the document, act, or information of any combination thereof was publicly available, known to the public, part of the general knowledge in the art, or was known to be relevant to solve any problem at the time of priority.

The disclosures of all publications cited above are expressly incorporated herein by reference, each in its entirety, to the same extent as if each were incorporated by reference individually.

While there has been described and illustrated specific embodiments of compositions and methods for treatment of stroke, it will be apparent to those skilled in the art that variations and modifications are possible without deviating from the broad spirit and principle of the present invention. It is also to be understood that the following claims are intended to cover all of the generic and specific features of the invention herein described, and all statements of the scope of the invention which, as a matter of language, might be said to fall therebetween.

What is claimed is:

1. A method of treatment of cerebral ischemia in a patient comprising:
    selecting for CD 117$^+$ cells from menstrual blood to form an isolated menstrual blood-derived stem cell enriched cell population;
    culturing the menstrual blood-derived stem cell enriched cell population to form an expanded, isolated menstrual blood-derived stem cell population;
    selecting the expanded, isolated menstrual blood-derived stem cell population for CXCR4 to form a menstrual blood-derived therapeutic; and
    administering a therapeutically effective amount of the menstrual blood-derived therapeutic into the patient.

2. The method of claim 1, wherein the isolated menstrual blood-derived stem cell enriched cell population was administered within 2 hours of stroke.

3. The method of claim 1, further comprising selecting adherent cells from the isolated menstrual blood-derived stem cell enriched cell population, wherein the adherent cells are selected by culturing the isolated menstrual blood-derived stem cell enriched cell population;
removing the non-adherent cells from the culture;
wherein the adherent cells remain in the isolated menstrual blood-derived stem cell enriched cell population.

4. The method of claim 1, wherein the isolated menstrual blood-derived stem cell enriched cell population was filtered with a 100 μm filter.

5. The method of claim 1, wherein the isolated menstrual blood-derived stem cell enriched cell population was treated with a plurality of antibiotics prior to administration into the patient.

6. The method of claim 1, wherein the isolated menstrual blood-derived stem cell enriched cell population excretes at least one trophic factor selected from the group consisting of vascular endothelial growth factor, brain-derived neurotrophic factor, and neurotrophin-3.

7. The method of claim 1, wherein the isolated menstrual blood-derived stem cell enriched cell population is administered intravenously or intracranially.

8. The method of claim 7, wherein the isolated menstrual blood-derived stem cell enriched cell population is implanted 0.5 mm anterior to the bregma, 2.8 mm lateral to midline, and 5.0 mm below the dural surface.

9. The method of claim 7, wherein the isolated menstrual blood-derived stem cell enriched cell population is administered into the jugular vein.

10. The method of claim 8, wherein the isolated menstrual blood-derived stem cell enriched cell population is administered at $4 \times 10^5$ cells.

11. The method of claim 9, wherein the isolated menstrual blood-derived stem cell enriched cell population is administered at $4 \times 10^6$ cells.

12. The method of claim 1, further comprising culturing the human menstrual blood-derived stem cell population in neural induction medium and retinoic acid.

13. The method of claim 12, wherein the human menstrual blood-derived stem cell population is cultured in DMEM/F12 supplemented with N2 and FGF-2.

* * * * *